United States Patent
Roh et al.

(10) Patent No.: US 12,029,434 B1
(45) Date of Patent: Jul. 9, 2024

(54) PATIENT MONITORING FOR SURGICAL PROCEDURES USING A WEARABLE ASSESSMENT DEVICE

(71) Applicant: IX Innovation LLC, Seattle, WA (US)

(72) Inventors: Jeffrey Roh, Seattle, WA (US); Justin Esterberg, Mesa, AZ (US); John Cronin, Jericho, VT (US); Seth Cronin, Essex Junction, VT (US); Michael John Baker, Georgia, VT (US)

(73) Assignee: IX Innovation LLC, Seattle, WA (US)

( * ) Notice: Subject to any disclaimer, the term of this patent is extended or adjusted under 35 U.S.C. 154(b) by 0 days.

(21) Appl. No.: 18/218,399

(22) Filed: Jul. 5, 2023

(51) Int. Cl.
```
A61B 34/30      (2016.01)
A61B 5/00       (2006.01)
A61B 17/128     (2006.01)
B25J 15/00      (2006.01)
G16H 40/63      (2018.01)
A61B 5/0205     (2006.01)
```

(52) U.S. Cl.
CPC .......... *A61B 17/128* (2013.01); *A61B 5/6801* (2013.01); *A61B 34/30* (2016.02); *B25J 15/0019* (2013.01); *G16H 40/63* (2018.01); *A61B 5/02055* (2013.01)

(58) Field of Classification Search
CPC . A61B 17/128; A61B 5/6801; A61B 5/02055; A61B 34/30
See application file for complete search history.

(56) References Cited

U.S. PATENT DOCUMENTS 11,357,582 B1 * 6/2022 Roh .................. G10L 13/02
11,583,361 B1 * 2/2023 Roh .................. A61B 90/98

\* cited by examiner

*Primary Examiner* — Vi X Nguyen
(74) *Attorney, Agent, or Firm* — Fish & Richardson P.C.

(57) ABSTRACT

The present disclosure provides a method for using a wearable device involved with the surgery of a patient preoperatively, intraoperatively, and postoperatively in which the patient condition is assessed and determines at least one medical wearable device. A profile is created for the patient that interacts with the wearable device and at least one condition is communicated preoperatively through the wearable device and the patient's profile is updated intraoperatively using the wearable device and postoperatively the wearable device communicates at least one second condition based on the updated profile.

13 Claims, 9 Drawing Sheets

FIG. 6

Figure 1:
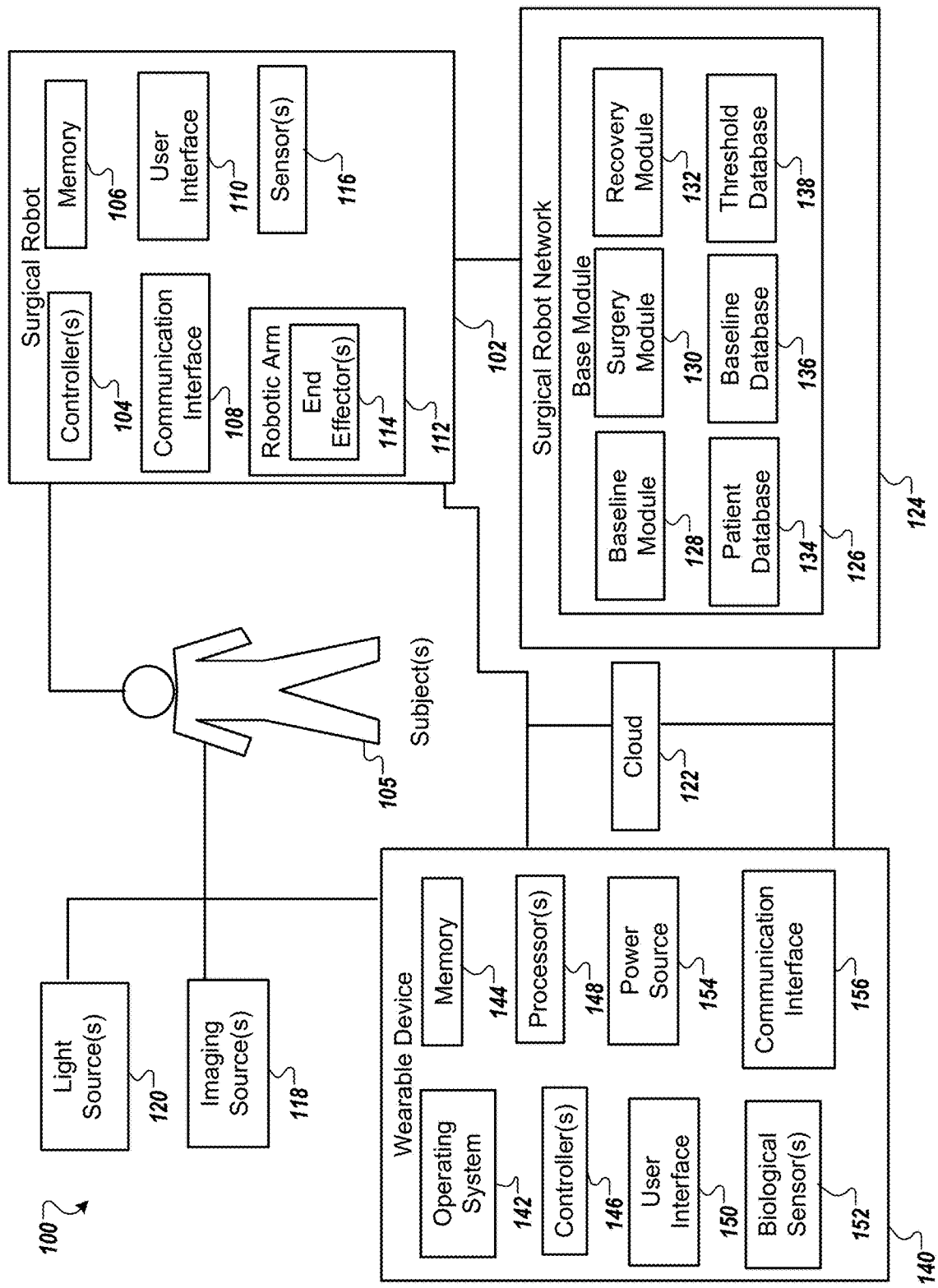

| Name | ID | High Pulse | Low Pulse | High Blood Pressure | Low Blood Pressure | High SpO2 | Low SpO2 |
|---|---|---|---|---|---|---|---|
| John Smith | JS1234 | 100 bpm | 60 bpm | 120/80 | 90/60 | 100% | 90% |
| . | . | . | . | . | . | . | . |
| . | . | . | . | . | . | . | . |
| . | . | . | . | . | . | . | . |

FIG. 7

| Name | ID | High Pulse | Low Pulse | High Blood Pressure | Low Blood Pressure | High SpO2 | Low SpO2 |
|---|---|---|---|---|---|---|---|
| John Smith | JS1234 | 90 bpm | 60 bpm | 120/80 | 90/60 | 100% | 93% |
| ⋮ | ⋮ | ⋮ | ⋮ | ⋮ | ⋮ | ⋮ | ⋮ |
| ⋮ | ⋮ | ⋮ | ⋮ | ⋮ | ⋮ | ⋮ | ⋮ |
| ⋮ | ⋮ | ⋮ | ⋮ | ⋮ | ⋮ | ⋮ | ⋮ |

FIG. 8

PATIENT MONITORING FOR SURGICAL PROCEDURES USING A WEARABLE ASSESSMENT DEVICE

FIELD OF THE DISCLOSURE

The present disclosure is generally related to uses of a wearable patient monitoring device involved with the surgery of a patient preoperatively, intraoperatively, and post-operatively.

BACKGROUND

Advanced surgical systems include many different types of equipment to monitor and anesthetize the patient, assist the surgeon in performing surgical tasks, and maintain the environment of the operating room.

Surgical procedures have been planned for new patients based on historical data and patient cohorts who have previously undergone similar procedures. It has been difficult to tailor procedures to the conditions of individual patients. Then, patients have often experienced post-surgical effects that range from typical discomfort to serious complications. It has been difficult to determine a patient's recovery from a surgical procedure without having the patient's data monitored and analyzed to determine if the patient is experiencing normal discomforts, performing the correct recovery process as planned by the medical professionals, or is experiencing serious complications based on medications, infections, or other more serious complications.

SUMMARY

This specification generally describes, systems, methods, devices, and other techniques for implementing a wearable device to monitor a condition of a surgical patient pre-operatively, intraoperatively, and/or post-operatively.

Some embodiments include a method for monitoring a subject. The method includes receiving a sensor data set for the subject, the sensor data set may include one or more patient metrics that indicate one or more biological conditions of the subject and that are based on signals produced by one or more biological sensors included in a wearable device on the subject, the sensor data received at a first time that is at least a pre-defined period of time ahead of a medical procedure scheduled for the subject. The method also includes determining that a current time is within the pre-defined period of time ahead of the medical procedure scheduled for the subject. The method also includes determining a set of patient metrics to use as a baseline data set for monitoring the subject during the medical procedure. The method also includes using the baseline data to assess the subject's condition during the medical procedure.

Some implementations can include one or more of the following optional features. The method may include: determining one or more procedure thresholds based on the baseline data, the one or more procedure thresholds include expected high and low values of the one or more patient metrics during the procedure. The baseline data includes data acquired during the pre-defined period of time ahead of the medical procedure on the procedure date and data acquired before the procedure date. The method may include: determining if a current time matches the procedure time; and sending, responsive to a determination that the current time matches the procedure time, a request to the wearable patient device for a procedure data set, the procedure data set including one or more patient metrics collected by the one or more biological sensors during the procedure time. The method may include: determining if the one or more patient metrics of the procedure data set are outside of the one or more procedure thresholds; and sending, responsive to a determination that one or more patient metrics are outside of the one or more procedure thresholds, instructions to a surgical robot, the instructions to the surgical robot include one or more intervention steps based on the one or more patient metrics that are outside of the one or more procedure thresholds. The one or more intervention steps include actuating one or more end effectors of the surgical robot to clamp an artery. The method may include: determining if a current time matches the procedure time; and sending, responsive to a determination that the current time matches the procedure time, a request to the wearable patient device for a procedure data set, the procedure data set including one or more patient metrics that correspond to a procedure type, the one or more metrics that correspond to the procedure type are collected during the procedure time. The method may include: determining if the one or more patient metrics of the procedure data set are outside of the one or more procedure thresholds; and sending, responsive to a determination that one or more patient metrics are outside of the one or more procedure thresholds, instructions to a surgical robot, the instructions to the surgical robot include one or more intervention steps based on the one or more patient metrics that are outside of the one or more procedure thresholds. The method may include: repeatedly sending requests to the wearable patient device for an updated procedure data set responsive to the determination that one or more patient metrics are outside of the one or more procedure thresholds; determining that the one or more patient metrics are within the one or more procedure thresholds; and sending, responsive to the determination that one or more patient metrics are within the one or more procedure thresholds, instructions to a surgical robot, the instructions to the surgical robot including stop instructions for the one or more intervention steps. The wearable patient device activates and collects data from the one or more biological sensors based on the requested one or more patient metrics that correspond to the procedure type. The method may include: receiving surgical robot sensor data that is acquired by one or more sensors of the surgical robot; comparing the surgical robot sensor data to the procedure data; determining that the one or more patient metrics are within the one or more procedure thresholds; and sending, responsive to the determination that one or more patient metrics are within the one or more procedure thresholds, instructions to a surgical robot, the instructions to the surgical robot include stop instructions for the one or more intervention steps. The method may include: determining if a current time is after the procedure time on the procedure date; and determining one or more recovery thresholds based on the baseline data set and a procedure data set, the one or more recovery thresholds include high and low values of the one or more patient metrics. The method may include: sending, responsive to a determination that the current time is after the procedure time, a request to the wearable patient device for a recovery data set, the recovery data set including one or more patient metrics that are collected after the procedure time. The method may include: determining if the one or more patient metrics of the recovery data set are outside of the one or more recovery thresholds; and sending, responsive to a determination that one or more patient metrics are outside of the one or more recovery thresholds, instructions to a surgical robot, the instructions to the surgical robot include one or more intervention steps based on the one or more patient metrics that are outside of the one or more recovery thresholds. The method may include: repeatedly sending requests to the wearable patient device for an updated recovery data set responsive to the determination that one or more patient metrics are outside of the one or more recovery thresholds; determining that the one or more patient metrics are within the one or more recovery thresholds; and sending, responsive to the determination that one or more patient metrics are within the one or more recovery thresholds, instructions to a surgical robot, the instructions to the surgical robot include stop instructions for the one or more intervention steps. The method may include, determining that the one or more patient metrics are within the one or more recovery thresholds; and sending, responsive to the determination that one or more patient metrics are within the one or more recovery thresholds, instructions to the wearable patient device to collect baseline data. Implementations of the described techniques may include hardware, a method or process, or computer software on a computer-accessible medium.

Some embodiments include a method for monitoring data of a subject. The method also includes receiving a sensor data set for the subject, the sensor data set may include one or more patient metrics that indicate one or more biological conditions of the subject and that are based on signals produced by one or more biological sensors included in a wearable device on the subject, the sensor data received at a first time that is at least a pre-defined period of time ahead of a medical procedure scheduled for the subject. The method also includes identifying a medical procedure date from a patient profile associated with the wearable patient device. The method also includes determining that a current time is within the pre-defined period of time ahead of the medical procedure scheduled for the subject. The method also includes determining a set of patient metrics to use as a baseline data set for monitoring the subject during the medical procedure. The method also includes determining if a current time matches the medical procedure time. The method also includes sending, responsive to a determination that the current time matches the medical procedure time, a request to the wearable patient device for a procedure data set, the procedure data set including one or more patient metrics collected during the procedure time. The method also includes determining if the one or more patient metrics of the procedure data set are outside of one or more procedure thresholds. The method also includes sending, responsive to a determination that one or more patient metrics are outside of the one or more procedure thresholds, instructions to a surgical robot, the instructions to the surgical robot include one or more intervention steps based on the one or more patient metrics that are outside of the one or more procedure thresholds.

Some implementations can include one or more of the following optional features. The method where the wearable patient device activates and collects data from one or more sensors based on the requested one or more patient metrics that correspond to a procedure type. The method may include: repeatedly sending requests to the wearable patient device for an updated procedure data set responsive to the determination that one or more patient metrics are outside of the one or more procedure thresholds; determining that the one or more patient metrics are within the one or more procedure thresholds; and sending, responsive to the determination that one or more patient metrics are within the one or more procedure thresholds, instructions to a surgical robot, the instructions to the surgical robot include stop instructions for the one or more intervention steps. The method may include: determining if a current time is after the procedure time on the procedure date; and determining one or more recovery thresholds based on the baseline data set and a procedure data set, the one or more recovery thresholds include high and low values of the one or more patient metrics. Implementations of the described techniques may include hardware, a method or process, or computer software on a computer-accessible medium.

Non-limiting examples of surgical equipment that may be used or improved by the techniques described in this specification are provided for reference.

Vital signs monitor refers to medical diagnostic instruments and in particular to a portable, battery powered, multi-parametric, vital signs monitoring device that can be used for both ambulatory and transport applications as well as bedside monitoring. These devices can be used with an isolated data link to an interconnected portable computer allowing snapshot and trended data from the monitoring device to be printed automatically and also allowing default configuration settings to be downloaded to the monitoring device. The monitoring device is capable of use as a stand-alone unit as well as part of a bi-directional wireless communications network that includes at least one remote monitoring station. A number of vital signs monitoring devices are known that are capable of measuring multiple physiologic parameters of a patient wherein various sensor output signals are transmitted either wirelessly or by means of a wired connection to at least one remote site, such as a central monitoring station. A vital signs monitor can be integrated into the embodiments in a variety of manners.

Heart rate monitor refers to the sensor(s) and/or sensor system(s) that can be applied in the context of monitoring heart rates. Embodiments are intended to measure, directly or indirectly, any physiological condition from which any relevant aspect of heart rate can be gleaned. For example, some of the embodiments measure different or overlapping physiological conditions to measure the same aspect of heart rate. Alternatively, some embodiments measure the same, different, or overlapping physiological conditions to measure different aspects of heart rate, i.e., number of beats, strength of beats, regularity of beats, beat anomalies, etc. A heart rate monitor can be integrated into the embodiments in a variety of manners.

Pulse oximeter or SpO2 Monitor refers to a plethysmograph or any instrument that measures variations in the size of an organ or body part on the basis of the amount of blood passing through or present in the part. An oximeter is a type of plethysmograph that determines the oxygen saturation of the blood. One common type of oximeter is a pulse oximeter. A pulse oximeter is a medical device that indirectly measures the oxygen saturation of a patient's blood (as opposed to measuring oxygen saturation directly through a blood sample) and changes in blood volume in the skin. A pulse oximeter may include a light sensor that is placed at a site on a patient, usually a fingertip, toe, forehead, or earlobe, or in the case of a neonate, across a foot. Light, which may be produced by a light source integrated into the pulse oximeter, containing both red and infrared wavelengths is directed onto the skin of the patient and the light that passes through the skin is detected by the sensor. The intensity of light in each wavelength is measured by the sensor over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation. A pulse oximeter can be integrated into the embodiments in a variety of manners.

End Tidal CO2 monitor or capnography monitor refers to an instrument which is used for measurement of level of carbon dioxide (referred to as end tidal carbon dioxide, ETCO2) that is released at the end of an exhaled breath. End Tidal CO2 monitor or capnography monitor is widely used in anesthesia and intensive care. ETCO2 can be calculated by plotting expiratory CO2 with time. Further, ETCO2 monitor plays a very crucial role for the measurement of applications such as Cardiopulmonary Resuscitation (CPR), Airway assessment, Procedural sedation and analgesia, Pulmonary diseases such as obstructive pulmonary disease, pulmonary embolism, etc., heart failure, metabolic disorders, etc. The instrument can be configured as side stream (diverting) or mainstream (non-diverting). Diverting device transports, a portion of a patient's respired gases from the sampling site to the sensor while non-diverting device does not transport gas away. Also, measurement by the instrument is based on the absorption of infrared light by carbon dioxide; where exhaled gas passes through a sampling chamber containing an infrared light source and photodetector on both sides. Based on the amount of infrared light reaching the photodetector, the amount of carbon dioxide present in the gas can be calculated. An ETCO2 monitor or capnography monitor can be integrated into the embodiments in a variety of manners.

Blood pressure monitor refers to any instrument that measures blood pressure, particularly in arteries. Blood pressure monitors use a non-invasive technique (by external cuff application) or an invasive technique (by a cannula needle inserted in artery, used in operating theatre) for measurement, with non-invasive measurement being widely used. The non-invasive method (referred to as sphygmomanometer further) works by measurement of force exerted against arterial walls during ventricular systole (i.e., systolic blood pressure, occurs when heart beats and pushes blood through the arteries) and ventricular diastole (i.e., diastolic blood pressure, occurs when heart rests and is filling with blood) thereby measuring systole and diastole, respectively. It can be of three types automatic/digital, manual (aneroid-dial), and manual (mercury-column). The sphygmomanometer may include a bladder, a cuff, a pressure meter, a stethoscope, a valve, and a bulb. The cuff then inflates until it fits tightly around your arm, cutting off your blood flow, and then the valve opens to deflate it. It operates by inflating a cuff tightly around the arm, as the cuff reaches the systolic pressure, blood begins to flow around your artery, and creating a vibration which is detected by the meter, which records your systolic pressure. This systolic pressure is recorded. The techniques used for measurement may be: auscultatory or oscillometric. A blood pressure monitor can be integrated into the embodiments in a variety of manners.

Body temperature monitor refers to any instrument which is used for measurement of body temperature. The instrument can measure the temperature invasively or non-invasively by placement of sensor into organs such as bladder, rectum, esophagus, tympanum, esophagus, etc., and mouth, rectum, armpit, etc., respectively. The sensors are of two types: contact and non-contact. It can be measured in two forms: core temperature and peripheral temperature. Temperature measurement can be done by these sensing technologies: thermocouples, resistive temperature devices (RTDs, thermistors), infrared radiators, bimetallic devices, liquid expansion devices, molecular change-of-state, and silicon diodes. A thermometer which is a commonly used instrument for the measurement of temperature consists of a temperature sensing element (e.g., temperature sensor) and a means for converting to a numerical value. A blood temperature monitor can be integrated into the embodiments in a variety of manners.

Respiration rate or breathing rate is the rate at which breathing occurs and is measured by a number of breaths a person takes per minute. The rate is usually measured when a person is at rest and simply involves counting the number of breaths for one minute by counting how many times the chest rises. Normal respiration rates for an adult person at rest are in the range: 12 to 16 breaths per minute. A variation can be an indication of an abnormality/medical condition or a patient's demographic parameters. Hypoxia is a condition with low levels of oxygen in the cells and hypercapnia is a condition in which high levels of carbon dioxide in the bloodstream. Pulmonary disorders, asthma, anxiety, pneumonia, heart diseases, dehydration, drug overdose are some of the abnormal conditions which can bring a change to the respiration rate, thereby increasing or reducing the respiration rate from normal levels. Respiratory rate can be integrated into the embodiments in a variety of manners.

An electrocardiogram abbreviated as EKG or ECG refers to a representation of the electrical activity of the heart (graphical trace of voltage versus time) which is done by placement of electrodes on skin/body surface. The electrodes capture the electrical impulse which travels through the heart causing systole and diastole or the pumping of the heart. This impulse gives a lot of information related to the normal functioning of the heart and the production of impulses. A change may occur due to medical conditions such as arrhythmias (tachycardia where the heart rate becomes faster and bradycardia where the heart rate becomes slower), coronary heart disease, heart attacks, cardiomyopathy. The instrument used for the measurement of the electrocardiogram is called an electrocardiograph which measures the electrical impulses by the placement of electrodes on the surface of the body and represents the ECG by a PQRST waveform. PQRST wave is read as: P wave which represents the depolarization of the left and right atrium and corresponding to atrial contraction, QRS complex indicates ventricular depolarization and represents the electrical impulse as it spreads through the ventricles; T wave indicates ventricular repolarization and follows the QRS complex. An electrocardiogram can be integrated into the embodiments in a variety of manners.

Neuromonitoring also called Intraoperative neurophysiological monitoring (abbreviated as IONM) refers to an assessment of functions and changes in the brain, brainstem, spinal cord, cranial nerves, and peripheral nerves during a surgical procedure on these organs. It includes both continuous monitoring of neural tissue as well as the localization of vital neural structures. IONM measures changes in these organs which are indicative of irreversible damage, injuries in the organs, aiming at reducing the risk of neurological deficits after operations involving the nervous system. This has also been found to be effective in localization of anatomical structures, including peripheral nerves and sensorimotor cortex, which help in guiding the surgeon during dissection. Electrophysiological modalities which are employed in neuromonitoring are an extracellular single unit and local field recordings (LFP), Somatosensory Evoked Potential (SSEP), transcranial electrical motor evoked potentials (TCeMEP), Electromyography (EMG), electroencephalography (EEG), and auditory brainstem response (ABR). The use of neurophysiological monitoring during surgical procedures requires specific anesthesia techniques to avoid interference and signal alteration due to anesthesia. Neuromonitoring can be integrated into the embodiments in a variety of manners.

Motor Evoked Potential abbreviated as MEP refers to electrical signals which are recorded from descending motor pathways or muscles following stimulation of motor pathways within the brain. MEP may be calculated by measurement of the action potential which is elicited by non-invasive stimulation of the motor cortex through the scalp. MEP is a widely used technique for intraoperative monitoring and neurophysiological testing of the motor pathways specifically during spinal procedures. The technique of monitoring for measurement of MEP can be defined based on some of the parameters like a site of stimulation (motor cortex or spinal cord), method of stimulation (electrical potential or magnetic field), and site of recording (spinal cord or peripheral mixed nerve and muscle). The target site may be stimulated by the use of electrical or magnetic means. MEP can be integrated into the embodiments in a variety of manners.

Somatosensory evoked potential abbreviated as SSEP or SEP refers to the electrical signals which are elicited by the brain and the spinal cord in response to sensory stimulus or touch. SSEP is one of the most frequently used techniques for intraoperative neurophysiological monitoring in spinal surgeries. The method proves to be very reliable which allows for continuous monitoring during a surgical procedure. However, accuracy may be a concern at times in measurement. The sensor stimulus which is commonly given to the organs may be auditory, visual, or somatosensory SEPs and applied on the skin, peripheral nerves of the upper limb, lower limb, or scalp. The stimulation technique may be mechanical (widely used), or electrical (found to give larger and more robust responses), intraoperative spinal monitoring modality. Somatosensory evoked potential can be integrated into the embodiments in a variety of manners.

Electromyography abbreviated as EMG refers to the evaluation and recording of electrical signals or electrical activity of the skeletal muscles. Electromyography instrument or Electromyograph or Electromyogram, the instrument for the measurement of the EMG activity works on a technique used for a recording of electrical activity produced by skeletal muscles and evaluation of the functional integrity of individual nerves. The nerves which are monitored by the EMG instrument may be intracranial, spinal, or peripheral nerves. The electrodes which may be used for the acquisition of signals may be invasive and non-invasive electrodes. The technique used for measurement may be spontaneous or triggered. Spontaneous EMG refers to the recording of myoelectric signals during surgical manipulation such as compression, stretching, or pulling of nerves produces; and does not perform external stimulation. Spontaneous EMG may be recorded by the insertion of a needle electrode. Triggered EMG refers to the recording of myoelectric signals during stimulation of target site such as pedicle screw with incremental current intensities. Electromyography can be integrated into the embodiments in a variety of manners.

Electroencephalography abbreviated as EEG refers to the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp where each pair of electrodes transmit a signal to one or more recording channels. It is one of the oldest and most commonly utilized modalities for intraoperative neurophysiological monitoring and assessing cortical perfusion and oxygenation during a variety of vascular, cardiac, and neurosurgical procedures. The waves produced by EEG are Alpha, Beta, Theta, and Delta. Electroencephalography can be integrated into the embodiments in a variety of manners.

Medical visualization systems refer to visualization systems that are used for visualization and analysis of objects (preferably three-dimensional (3D) objects). Medical visualization systems include the selection of points at surfaces, selection of a region of interest, selection of objects. Medical visualization systems may be used for applications diagnosis, treatment planning, intraoperative support, documentation, educational purpose. Medical visualization systems may consist of microscopes, endoscopes/arthroscopes/laparoscopes, fiber optics, surgical lights, high-definition monitors, operating room cameras, etc. 3D visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times. Medical visualization systems can be integrated into the embodiments in a variety of manners.

A microscope refers to an instrument that is used for viewing samples & objects that cannot be seen with an unaided eye. A microscope may have components eyepiece, objective lenses, adjustment knobs, stage, illuminator, condenser, diaphragm. A microscope works by manipulating how light enters the eye using a convex lens, where both sides of the lens are curved outwards. When light reflects off of an object being viewed under the microscope and passes through the lens, it bends towards the eye. This makes the object look bigger than it is. A microscope may be of types compound (light illuminated and the image seen with the microscope is two dimensional), dissection or stereoscope (light illuminated and image seen with the microscope is three dimensional), confocal (laser-illuminated and image seen with the microscope on a digital computer screen), Scanning Electron abbreviated as SEM (electron illuminated and image seen with the microscope in black and white), Transmission Electron Microscope abbreviated as TEM (electron illuminated and image seen with the microscope is the high magnification and high resolution). A microscope can be integrated into the embodiments in a variety of manners.

Endoscopes or arthroscopes or laparoscopes refer to minimally invasive surgical techniques where procedures are performed by performing minimal incision in the body. An Endoscope refers to an instrument to visualize, diagnose, and treat problems inside hollow organs where the instrument is inserted through natural body openings such as the mouth or anus. An endoscope may perform a procedure as follows: scope with a tiny camera attached to a long, thin tube is inserted. The doctor moves it through a body passageway or opening to see inside an organ. It can be used for diagnosis and surgery (such as for removing polyps from the colon). Arthroscope refers to an instrument to visualize, diagnose, and treat problems inside a joint by a TV camera inserted through small portals/incisions and perform procedures on cartilage, ligaments, tendons, etc. An endoscope may perform the procedure as follows: a surgeon makes a small incision in a patient's skin and inserts a pencil-sized instrument with a small lens and lighting system to magnify the target site (joint) and viewing of the interior of the joint by means of a miniature television camera and performing procedure. Endoscope refers to an instrument to visualize, diagnose, and treat problems inside soft organs like the abdomen and pelvis by a TV camera inserted through small portals/incisions and perform procedures. Endoscopes/arthroscopes/laparoscopes or minimally invasive surgery techniques can be integrated into the embodiments in a variety of manners.

Fiber optics refers to flexible, transparent fiber made by drawing glass (silica) or plastic to a diameter slightly thicker than that of a human hair. Fiber optics are arranged in bundles called optical cables and used to transmit light signals over long distances. Fiber optics are used most often as a means to transmit light between the two ends of the fiber and find wide usage in the medical field. Traditional surgery requires sizable and invasive incisions to expose internal organs and operate on affected areas and with fiber optics much smaller surgical incisions can be performed. Fiber optics contain components core, cladding, buffer coating. Fiber optics may be inserted in hypodermic needles and catheters, endoscope, operation theatres, ophthalmology, dentistry tools. Fiber optics sensors comprise a light source, optical fiber, external transducer, and photodetector. Fiber-optic sensors may be intrinsic or extrinsic. Fiber optics sensors may be categorized into four types physical, imaging, chemical, and biological. Fiber optics can be integrated into the embodiments in a variety of manners.

Surgical lights also referred to as operating light refers to an instrument that performs illumination of a local area or cavity of the patient. Surgical lights play an important role in illumination before, during, and after a medical procedure. Surgical lights may be categorized by lamp type as conventional (incandescent) and LED (light-emitting diode). Surgical lights may be categorized by mounting configuration as ceiling-mounted, wall-mounted, or floor stand. Surgical lights may be categorized by type as tungsten, quartz, and/or xenon halogens and light-emitting diodes (LEDs). Surgical lights include sterilizable handles which allow the surgeon to adjust light positions. Some important factors affecting surgical lights may be illumination, shadow management (cast shadows and contour shadows), the volume of light, heat management, fail-safe surgical lighting. Surgical lights can be integrated into the embodiments in a variety of manners.

High definition monitors refer to a display in which a clearer picture than possible with low-definition, low-resolution screens. High-definition monitors have a higher density of pixels per inch than past standard TV screens. Resolution for high definition monitors may be 1280×720 pixels or more. Full HD-1920×1080, Quad HD-2560×1440, 4K-3840×2160, 8K-7680×4320 pixels. High definition monitor may operate in progressive or interlaced scanning mode. High definition monitors used in medical applications may offer the following advantages improved visibility and allows for precise and safe surgery, rich color reproduction and provides suitable colors for each clinical discipline, better visibility, and operability with a large screen and electronic zoom, higher image quality in low light conditions, high contrast at high spatial frequencies, twice as sensitive as conventional sensors, easier determination of tissue boundaries (fat, nerves, vessels, etc.), better visualization of blood vessels and lesions. High definition monitors can be integrated into the embodiments in a variety of manners.

Operating room cameras refer to cameras that collect images from 360 degrees, and sensors that monitor both the operating room and people in it. Operating room cameras consist of cameras that are equipped in system and perform recording to give a bird's-eye view to the surgical team. Some cameras are on devices that surgeons insert through small incisions or orifices to see what they are doing during minimally invasive surgery. Operating room cameras may perform recording for this purpose: educational purposes: example—to broadcast a live feed of a surgical demonstration to a remote audience, to collect authentic footage for edited, instructional videos on a surgical technique or procedure; to facilitate video enhanced debriefing and coaching, or to formally assess surgical skills. Operating room cameras can be integrated into the embodiments in a variety of manners.

Surgical tower refers to an instrument used for performing minimally invasive surgery or surgery which is performed by creating small incisions in the body, therefore they are also referred to as minimally invasive devices or minimally invasive access devices. The procedure of performing minimally invasive surgery may be referred to as minimally invasive procedure or minimally invasive surgery, abbreviated as MIS. MIS is a safe, less invasive, and precise surgical procedure. Some of the advantages offered by surgical towers may be small incisions, less pain, low risk of infection, short hospital stays, quick recovery time, less scarring, and reduced blood loss. Some medical procedures where surgical towers are useful and are widely used may be lung procedures, gynecological, head and neck, heart, and urological conditions. MIS may be robotic or non-robotic/endoscopic. MIS may include the following: endoscopic, laparoscopic, arthroscopic, natural orifice intraluminal, and natural orifice transluminal procedures. A surgical tower access device may be designed as an outer sleeve and an inner sleeve that telescoping or slidably engages with one another. When a telescope is used to operate on the abdomen, the procedure is called laparoscopy. Surgical towers typically include access to a variety of surgical tools, such as, for example, electrocautery, radiofrequency, lasers, sensors, etc. A surgical tower can be integrated into the embodiments in a variety of manners.

Electrocautery refers to an instrument that is used for burning a part of the body to remove or close off a part of it. Various physiological conditions or surgical procedures require the removal of body tissues and organs, a consequence of which is bleeding. In order to achieve hemostasis and for removing and sealing all blood vessels which are supplied to an organ after surgical incision an electrocautery instrument may be used. For example: after removing part of the liver for removal of tumor etc., blood vessels in the liver must be sealed individually. An electrocautery instrument may be used for sealing living tissue such as arteries, veins, lymph nodes, nerves, fats, ligaments, and other soft tissue structures. It may be used in applications surgery, tumor removal, nasal treatment, wart removal. Electrocautery may operate in modes two monopolar or bipolar. The electrocautery instrument may consist of a generator, a handpiece, and one or more electrodes. Electrocautery can be integrated into the embodiments in a variety of manners.

Radiofrequency (RF) is used in association with minimally invasive surgery devices. The radiofrequency (RF) may be used for the treatment of skin by delivering it to the skin through a minimally invasive tool (fine needles) which does not require skin excision. The RF may be used for real-time tracking of minimally invasive surgery devices such as laparoscopic instruments. The RF may provide radiofrequency ablation to a patient suffering from atrial fibrillation through smaller incisions made between the ribs.

The RF may be used to perform an endoscopic surgery on the body such as the spine by delivery of RF energy. Radiofrequency can be integrated into the embodiments in a variety of manners.

Laser is used in association with minimally invasive surgery devices. The laser may be used in minimally invasive surgeries with an endoscope. The laser is attached to the distal end of the endoscope and steers the laser at high speed by producing higher incision quality than existing surgical tools and minimizing damage to surrounding tissue. Laser may be used to perform minimally invasive surgeries using an endoscope, laparoscope in the lower and upper gastro-intestinal tract, eye, nose, and throat. Lasers are used in minimally invasive surgery to ablate soft tissues, such as a herniated spinal disc bulge. Laser can be integrated into the embodiments in a variety of manners.

Sensors are used in association with minimally invasive surgery devices. The sensor may be used in minimally invasive surgeries for tactile sensing of tool—tissue interaction forces. During minimally invasive surgeries field of view and workspace of tools are compromised due to the indirect access to the anatomy and lack of surgeon's hand-eye coordination. The sensors provide a tactile sensation to the surgeon by providing information of shape, stiffness, and texture of organ or tissue (different characteristics) to surgeon's hands through a sense of touch. This detection of a tumor through palpation, which exhibit a 'tougher' feel than healthy soft tissue, pulse felt from blood vessels, and abnormal lesions. The sensors may provide in output shape, size, pressure, softness, composition, temperature, vibration, shear, and normal forces. Sensor may be electrical or optical, consisting of capacitive, inductive, piezoelectric, piezoresistive, magnetic, and auditory. The sensors may be used in robotic, laparoscopic, palpation, biopsy, heart ablation, and valvuloplasty. Sensors can be integrated into the embodiments in a variety of manners.

Imaging systems refer to techniques or instruments which are used for the creation of images and visualization of the interior of a human body for diagnostic and treatment purposes. Imaging systems play a crucial role in every medical setting and can help in the screening of health conditions, diagnosing causes of symptoms, monitor health conditions. Imaging systems may include various imaging techniques such as X-ray, Fluoroscopy, Magnetic resonance imaging (MRI), Ultrasound, Endoscopy, Elastography, Tactile imaging, Thermography, Medical photography, and Nuclear medicine e.g., Positron emission tomography (PET). Some factors which may drive the market are cost and clinical advantages of medical imaging modalities, a rising share of ageing populations, increasing prevalence of cardiovascular or lifestyle diseases, increasing demand from emerging economies. Some factors which may inhibit the market are saturation in many segments, high costs, lack of trained personnel. Imaging systems can be integrated into the embodiments in a variety of manners.

X-ray refers to a medical imaging instrument that uses X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of x-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type of tissue the X-rays pass through and their densities. Some of the applications where X-rays are used may be bone fractures, infections, calcification, tumors, arthritis, blood vessel blockages, digestive problems, heart problems. The X-ray instrument may consist of components such as an x-ray tube, operating console, collimator, grids, detector, radiographic film, etc. An X-ray can be integrated into the embodiments in a variety of manners.

Magnetic resonance imaging abbreviated as MRI refers to a medical imaging instrument that uses powerful magnets for the creation of images of the interior of the human body for diagnostic and treatment purposes. Some of the applications where MRI may be used may be brain/spinal cord anomalies, tumors in the body, breast cancer screening, joint injuries, uterine/pelvic pain detection, heart problems. For the creation of the image by an MRI instrument, magnetic resonance is produced by powerful magnets which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by Mill sensors. The time taken by the protons for realignment with the magnetic field, and energy release is dependent on environmental factors and the chemical nature of the molecules. MRI may more widely suit for imaging of non-bony parts or soft tissues of the body. MRI may be less harmful as it does not use damaging ionizing radiation as in the X-ray instrument. MRI instrument may consist of magnets, gradients, radiofrequency system, computer control system. Some areas where imaging by Mill should be prohibited may be people with implants. MRI can be integrated into the embodiments in a variety of manners.

Computed tomography imaging abbreviated as CT refers to a medical imaging instrument that uses an X-ray radiation (i.e., X-ray range in the electromagnetic radiation spectrum) for the creation of cross-sectional images of the interior of the human body for diagnostic and treatment purposes. CT refers to a computerized x-ray imaging procedure in which a narrow beam of x-rays is aimed at a patient and quickly rotated around the body, producing signals that are processed by the machine's computer to generate cross-sectional images—or "slices"—of the body The CT instrument produces cross-sectional images of the body. Computed tomography instrument is different from an X-ray instrument as it creates 3-dimensional cross-sectional images of the body while X-ray creates 2-dimensional images of the body; the 3-dimensional cross-sectional images are created by taking images from different angles, which is done by taking a series of tomographic images from different angles. The different taken images are collected by a computer and digitally stacked to form a three-dimensional image of the patient. For creation of images by the CT instrument, a CT scanner uses a motorized x-ray source that rotates around the circular opening of a donut-shaped structure called a gantry while the x-ray tube rotates around the patient shooting narrow beams of x-rays through the body. Some of the applications where CT may be used may be blood clots, bone fractures, including subtle fractures not visible on X-ray, organ injuries. CT can be integrated into the embodiments in a variety of manners.

Stereotactic navigation systems refer to an instrument that uses patient imaging (e.g., CT, MRI) to guide surgeons in the placement of specialized surgical instruments and implants before and during a procedure. The patient images are taken to guide the physician before or during the medical procedure. The stereotactic navigation system includes a camera having infrared sensors to determine the location of the tip of the probe being used in the surgical procedure. This information is sent in real-time so that the surgeons have a clear image of the precise location of where they are working in the body. Stereotactic navigation systems may be framed (attachment of a frame to patient's head using screws or pins) or frameless (do not require the placement of a frame on the patient's anatomy). Stereotactic navigation systems may be used for diagnostic biopsies, tumor resection, bone preparation/implant placement, placement of electrodes, otolaryngologic, or neurosurgical procedures. Stereotactic navigation systems can be integrated into the embodiments in a variety of manners.

Ultrasound imaging also referred to as sonography or ultrasonography refers to a medical imaging instrument that uses ultrasound or sound waves (also referred to as acoustic waves) for the creation of cross-sectional images of the interior of the human body for diagnostic and treatment purposes. Ultrasound in the instrument may be produced by a piezoelectric transducer which produces sound waves and sends them into the body. The sound waves which are reflected are converted into electrical signals which are sent to an ultrasound scanner. Ultrasound instruments may be used for diagnostic and functional imaging. Ultrasound instruments may be used for therapeutic or interventional procedures. Some of the applications where ultrasound may be used are diagnosis/treatment/guidance during medical procedures e.g., biopsies, internal organs such as liver/kidneys/pancreas, fetal monitoring, etc., in soft tissues, muscles, blood vessels, tendons, joints. Ultrasound may be used for internal (transducer is placed in organs e.g., vagina) and external (transducer is placed on chest for heart monitoring or abdomen for the fetus). An ultrasound machine may consist of a monitor, keyboard, processor, data storage, probe, and transducer. Ultrasound can be integrated into the embodiments in a variety of manners.

Anesthesiology machine refers to a machine that is used to generate and mix medical gases like oxygen or air and anesthetic agents to induce and maintain anesthesia in patients. Anesthesiology machines deliver oxygen and anesthetic gas to the patient as well as filter out expiratory carbon dioxide. Anesthesia machine may perform following functions provides O2, accurately mix anesthetic gases and vapors, enable patient ventilation, and minimize anesthesia related risks to patients and staff. Anesthesia machine may consist of the following essential components a source of oxygen (O2), O2 flowmeter, vaporizer (anesthetics include isoflurane, halothane, enflurane, desflurane, sevoflurane, and methoxyflurane), patient breathing circuit (tubing, connectors, and valves), scavenging system (removes any excess anesthetics gases). Anesthesia machine may be divided into three parts the high pressure system, the intermediate pressure system, and the low-pressure system. The process of anesthesia starts with oxygen flow from pipeline or cylinder through the flowmeter, O2 flows through the vaporizer and picks up the anesthetic vapors, the O2-anesthetic mix then flows through the breathing circuit and into the patient's lungs, usually by spontaneous ventilation or normal respiration. The O2-anesthetic mix then flows through the breathing circuit and into the patient's lungs, usually by spontaneous ventilation or normal respiration. An anesthesiology machine can be integrated into the embodiments in a variety of manners.

Surgical bed is a bed equipped with mechanisms that can elevate or lower the entire bed platform, flex, or extend individual components of the platform, or raise or lower the head or the feet of the patient independently. Surgical bed may be an operation bed, cardiac bed, amputation Bed, fracture bed. Some essential components of a surgical bed may be bed sheet, woolen blanket, bath towel, bed block. Surgical beds can also be referred to as a postoperative bed, refers to a special type of bed made for the patient who is coming from the operation theatre or from another procedure that requires anesthesia. The surgical bed is designed in a manner that makes it easier to transfer an unconscious or weak patient from a stretcher/wheelchair to the bed. The surgical bed should protect bed linen from vomiting, bleeding, drainage, and discharges, provide warmth and comfort to the patient to prevent shock, provide necessary position, which is suitable for operation, protect patient from being chilled, prepared to meet any emergency. Surgical bed can be integrated into the embodiments in a variety of manners.

Disposable air warmer (also referred to as bair) refers to a convective temperature management system used in a hospital or surgery center to maintain a patient's core body temperature. The instrument consists of a reusable warming unit and a single-use disposable warming blankets for use during surgery and may also be used before and after surgery. The air warmer uses convective warming consisting of two components a warming unit and a disposable blanket. The air warmer filter air and then force warm air through disposable blankets which cover the patient. The blanket may be designed to use pressure points on the patient's body to prevent heat from reaching areas at risk for pressure sores or burns. The blanket may also include drain holes where fluid passes through the surface of the blanket to linen underneath which will reduce the risk of skin softening and reduce the risk of unintended cooling because of heat loss from evaporation. Disposable air warmer can be integrated into the embodiments in a variety of manners.

Sequential compression device abbreviated as SVD refers to an instrument that is used to help prevent blood clots in the deep veins of legs. The sequential compression device use cuffs around the legs that fill with air and squeeze your legs. This increases blood flow through the veins of your legs and helps prevent blood clots. A deep vein thrombosis (DVT) is a blood clot that forms in a vein deep inside the body. Some of the risks of using a DVT may be discomfort, warmth, or sweating beneath the cuff, skin breakdown, nerve damage, pressure injury. Sequential compression device can be integrated into the embodiments in a variety of manners.

Jackson frame refers to a frame or table which is designed for use in spine surgeries and may be used in a variety of spinal procedures in supine, prone, lateral positions in a safe manner. Two peculiar features of the Jackson table are no central table support and its ability to rotate the table through 180 degrees. The Jackson table is supported at both ends keeping the whole of the table free. This allows the visualization of trunk and major parts of extremities as well. The Jackson frame allows the patient to be slid from the cart onto the table in the supine position with appropriate padding placed. The patient is then strapped securely on the table. The Jackson frame can be integrated into the embodiments in a variety of manners.

Bed position controller refers to an instrument for controlling the position of the patient bed. Positioning a patient in bed is important for maintaining alignment and for preventing bed-sores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient may be in the following positions in a bed supine position, prone position, lateral position, sims position, fowler's position, semi-Fowler's position, orthopedic or tripod position, Trendelenburg position. Bed position controller can be integrated into the embodiments in a variety of manners.

Operating room environmental controls refers to control or maintenance of the environment in an operation theatre where procedures are performed to minimize the risk of airborne infection and provide a conducive environment for everyone in the operation theatre—surgeon, anesthesiologist, nurses & patient). Some factors which may contribute to poor quality in the environment of the operating room are temperature, ventilation, and humidity and they can lead to profound effects on the health of people in the operating room and work productivity. As an example: surgeons prefer a cool, dry climate since they work in bright, hot lights; anesthesia personnel prefer a warmer, less breezy climate; patient condition demands a relatively warm, humid, and quiet environment. Operating room environmental controls may control the environment by taking care of the following factors environmental humidity, infection, odor control. Humidity control may be done by controlling the temperature of anesthesia gases; Infection can be controlled by the use of filters to purify the air. Operating room environmental controls can be integrated into the embodiments in a variety of manners.

Heating, ventilation, and air conditioning (abbreviated as HVAC) refers to a system for regulating environment of indoor settings by moving air between indoor and outdoor areas, along with heating and cooling. HVAC may use a different combination of systems, machines, and technologies to improve comfort. HVAC may be necessary to maintain the environment of an operating room. HVAC for an operating room may be a traditional operating room (which may have a large diffuser array directly above the operating table) or a hybrid operating room (which may have monitors and imaging equipment that consume valuable ceiling space and complicate the design process). HVAC may consist of three main units heating unit (it may be a furnace or a boiler), a ventilation unit (it may be natural or forced), and an air conditioning unit (which may remove existing heat). HVAC may be made of components as air return, filter, exhaust outlets, ducts, electrical elements, outdoor unit, compressor, coils, and blower. The HVAC system may use central heating and AC systems that use a single blower to circulate air via internal ducts. Heating, ventilation, and air conditioning can be integrated into the embodiments in a variety of manners.

Air purification refers to a system for removing contaminants from the air in a room to improve indoor air quality. Air purification may be important in an operating room as surgical site infection may be a reason for high mortality and morbidity. The air purification system may deliver clean, filtered, contaminant-free air over the operating room table with diffuser, airflow, etc., to remove all infectious particles down and away from the patient. Air purification system may be air curtain, multi-diffuser array, or single large diffuser (based on laminar diffuser flow) or High-Efficiency Particulate Air filter. High-Efficiency Particulate Air filter referred to as HEPA filter protects from infection and contamination by a filter which is mounted at the terminal of the duct. HEPA filter may be mounted on the ceiling and deliver clean, filtered air in a flow to the room that provides a sweeping effect that pushes contaminants out via the return grilles that are usually mounted on the lower wall. Air purification can be integrated into the embodiments in a variety of manners.

Orthopedic tools also referred to as orthopedic instruments used for treatment and prevention of deformities and injuries of musculoskeletal system or skeleton, articulations, and locomotive system (i.e., set formed by skeleton, muscles attached to it and part of nervous system which controls the muscles). Major percentage of orthopedic tools are made of plastic. Orthopedic tools may be divided into the following specialties hand and wrist, foot and ankle, shoulder and elbow, arthroscopy, hip, and knee. Orthopedic tool may be fixation tools, relieving tools, corrective tools, compression-distraction tools. Fixation tool refers to a tool designed to restrict movements partially or completely in a joint, e.g., hinged splints (for preserving a certain range of movement in a joint), rigid splints. Relieving tool refers to a tool designed to relieve pressure on an ailing part by transferring support to healthy parts of an extremity, e.g., Thomas splint and the Voskoboinikova apparatus. Corrective tool refers to a tool designed to gradually correct a deformity, e.g., corsets, splints, orthopedic footwear, and insoles and other devices to correct abnormal positions of the foot. Compression-distraction tool refers to a tool designed to correct acquired or congenital deformities of the extremities, e.g., curvature, shortening, and pseudarthrosis such as Gudushauri. Fixation tools may be internal fixation tools (e.g., screws, plates) or external fixation tools (radius, tibia fracture fixation). Orthopedic tools may be bone-holding forceps, drill bits, nail pins, hammer staple, etc. Orthopedic tools can be integrated into the embodiments in a variety of manners.

Drill refers to a tool for making holes in bones for insertion of implants like nails, plates, screws, and wires. The drill tool functions by drilling cylindrical tunnels into bone. Drill may be used in orthopedics for performing medical procedures. Use of drill on bones may have some risks harm caused to bone, muscle, nerves, and venous tissues are wrapped by surrounding tissue, the drill does not stop immediately. Drills vary widely in speed, power, and size. Drill may be powered as electrical, pneumatic, or battery. Drills generally may work on speed below 1000 rpm in orthopedic. Temperature control of drill is an important aspect in the functioning of drill and is dependent on parameters rotation speed, torque, orthotropic site, sharpness of the cutting edges, irrigation, cooling systems. The drill may consist of components physical drill, cord power, electronically motorized bone drill, rotating bone shearing incision work unit. Drill can be integrated into the embodiments in a variety of manners.

Scalpel refers to a tool for slicing or cutting or osteotomy of bone during orthopedic procedure. The scalpel may be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate and performs cutting by an ultrasonically oscillating or forward/backward moving metal tip. Scalpel may prevent injuries caused by a drill in a spinal surgery such as complications such as nerve thermal injury, grasping soft tissue, tearing dura mater, and a mechanical injury may occur during drilling. Scalpel can be integrated into the embodiments in a variety of manners.

Stitches (also referred to as sutures) refers to a sterile, surgical thread used to repair cuts or lacerations and are used to close incisions or hold body tissues together after a surgery or an injury. Stitches may involve the use of a needle along with an attached thread. Stitches may be of type absorbable (the stitches automatically break down harmlessly in the body over time without intervention) and non-absorbable (the stitches do not automatically break down over time and must be manually removed if not left indefinitely). Stitches may be of type based on material monofilament, multifilament, and barb. Stitches may be classified based on size. Stitches may be of type based on material synthetic and natural. Stitches may be of type based on coating coated and un-coated. Stitches can be integrated into the embodiments in a variety of manners.

Stapler refers to a tool for fragment fixation when interfragmental screw fixation is not easy. When there is vast damage and bone is broken into fragments then staples can be used between these fragments for internal fixation and bone reconstruction. For example, they may be used around joints as in ankle and foot surgeries, in cases of soft tissue damage, to attach tendons or ligaments to the bone for reconstruction surgery. Stapler may be made of surgical grade stainless steel or titanium and they are thicker, stronger, and larger. The stapler can be integrated into the embodiments in a variety of manners.

Equipment refers to a set of articles, tools, or objects which help to implement or achieve an operation or activity. A medical equipment refers to an article, instrument, apparatus, or machine used for diagnosis, prevention, or treatment of a medical condition or disease or detection, measurement, restoration, correction, or modification of structure/function of the body for some health purpose. The medical equipment may perform functions invasively or non-invasively. The medical equipment may consist of components sensor/transducer, signal conditioner, display, data storage unit, etc. The medical equipment works by taking a signal from a measurand/patient, a transducer for converting one form of energy to electrical energy, signal conditioner such as an amplifier, filters, etc., to convert the output from the transducer into an electrical value, display to provide a visual representation of measured parameter or quantity, a storage system to store data which can be used for future reference. A medical equipment may perform any function of diagnosis or provide therapy, for example, the equipment delivers air/breaths into the lungs and moves it out of the lungs and out of lungs, to a patient who is physically unable to breathe, or breaths insufficiently. A medical equipment can be integrated into the embodiments in a variety of manners.

Ventilator (also referred to as a respirator) refers to an instrument that provides a patient with oxygen when they are unable to breathe on their own. The ventilator is required when a person is not able to breathe on their own. The ventilator may perform a function of pushing air into the lungs and allows it to come back out, gently like lungs when they are working. Ventilator functions by delivery of positive pressure to force air into your lungs, while usual breathing uses negative pressure by the opening of the mouth, and air flows in. The machine uses positive pressure to force air into your lungs. A ventilator may be required during surgery or after surgery. A ventilator may be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator may be used with a face mask (non-invasive ventilation, where the ventilation is required for a shorter duration of time) or with a breathing tube also referred to as an endotracheal tube (invasive ventilation, where the ventilation is required for a longer duration of time). A ventilator use may have some risks such as infections, fluid build-up, muscle weakness, lung damage, etc. A ventilator may be operated in modes ACV, SIMV, PCV, PSV, PCIRV, APRV, etc. A ventilator may have components gas delivery system, power source, control system, safety feature, gas filter, monitor. A ventilator can be integrated into the embodiments in a variety of manners.

Continuous positive airway pressure abbreviated as CPAP refers to an instrument which used for the treatment of sleep apnea disorder in a patient. Sleep apnea refers to a disorder in which breathing repeatedly stops and starts while a patient is sleeping, often because throat/airways briefly collapse or something temporarily blocks them and may lead to serious health problems, such as high blood pressure and heart trouble. Continuous positive airway pressure instrument helps the patient with sleep apnea to breathe more easily during sleep by sending a steady flow of oxygen into the nose and mouth during sleep, which keeps the airways open and helps to breathe normally. The CPAP machine may work by a compressor/motor which generates a continuous stream of pressurized air which travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP may have a nasal pillow mask, nasal mask, or full mask. CPAP instrument may consist of components a motor, a cushioned mask, a tube that connects the motor to the mask, a headgear frame, adjustable straps. The essential components may be a motor, a cushioned mask, a tube that connects the motor to the mask. Continuous positive airway pressure instruments can be integrated into the embodiments in a variety of manners.

Consumables refer to necessary supplies for health systems to provide care within a hospital or surgical environment. Consumables may include gloves, gowns, masks, syringes, needles, sutures, staples, tubing, catheters, and adhesives for wound dressing, in addition to other tools needed by doctors and nurses to provide care. Depending on the device mechanical testing may be carried out in tensile, compression or flexure, in dynamic or fatigue, or impact or with the application of torsion. Consumables may be disposable (are time-saving, no risk of healthcare-associated infections, cost-efficient) or sterilizable (cross-contamination, risk of surgical site infections, sterilization). Consumables can be integrated into the embodiments in a variety of manners.

Robotic systems refer to systems that provide intelligent services and information by interacting with their environment, including human beings, via the use of various sensors, actuators, and human interfaces. These are employed for automating processes in a wide range of applications, ranging from industrial (manufacturing), domestic, medical, service, military, entertainment, space, etc. The adoption of robotic systems provides several benefits, including efficiency and speed improvements, lower costs, and higher accuracy. Performing medical procedures with the assistance of robotic technology are referred to as medical robotic systems. The medical robotic system market can be segmented by product type into Surgical Robotic Systems, Rehabilitative Robotic Systems, Non-invasive Radiosurgery Robots, Hospital & Pharmacy Robotic Systems. Robotic technologies have offered valuable enhancements to medical or surgical processes through improved precision, stability, and dexterity. Robots in medicine help by relieving medical personnel from routine tasks, and by making medical procedures safer and less costly for patients. They can also perform accurate surgery in tiny places and transport dangerous substances. Robotic surgeries are performed using tele-manipulators, which use the surgeon's actions on one side to control the "effector" on the other side. A medical robotic system ensures precision and may be used for remotely controlled, minimally-invasive procedures. The systems comprise computer-controlled electromechanical devices that work in response to controls manipulated by the surgeons. Robotic systems can be integrated into the embodiments in a variety of manners.

An Electronic Health Record (EHR) refers to a digital record of a patient's health information, which may be collected and stored systematically over time. It is an all-inclusive patient record and could include demographics, medical history, history of present illness (HPI), progress notes, problems, medications, vital signs, immunizations, laboratory data, and radiology reports. A computer software is used to capture, store, and share patient data in a structured way. The EHR may be created and managed by authorized providers and can make health information instantly accessible to authorized providers across practices and health organizations—such as laboratories, specialists, medical imaging facilities, pharmacies, emergency facilities, etc. The timely availability of EHR data can enable healthcare providers to make more accurate decisions and provide better care to the patients by effective diagnosis and reduced medical errors. Besides providing opportunities to enhance patient care, it may also be used to facilitate clinical research by combining all patients' demographics into a large pool. For example, the EHR data can support a wide range of epidemiological research on the natural history of disease, drug utilization, and safety, as well as health services research. The EHR can be integrated into the embodiments in a variety of manners.

Equipment tracking systems, such as RFID, refers to a system that tags an instrument with an electronic tag and tracks it using the tag. Typically, this could involve a centralized platform that provides details such as location, owner, contract, and maintenance history for all equipment in real-time. A variety of techniques can be used to track physical assets, including Radio-frequency Identification (RFID), Global Positioning System (GPS), Bluetooth Low Energy (BLE), barcodes, Near-Field Communication (NFC), Wi-Fi, etc. The equipment tracking system comprises the hardware components, such as RFID tags, GPS trackers, barcodes, and QR codes. The hardware component is placed on the asset, and it communicates with the software (directly or via a scanner), providing it with data about the asset's location and properties. An equipment tracking system uses electromagnetic fields to transmit data from an RFID tag to a reader. Reading of RFID tags may be done by portable or mounted RFID readers. RFID may be very short for low frequency or high frequency for ultra-high frequency. Managing and locating important assets is a key challenge for tracking medical equipment. Time spent searching for critical equipment can lead to expensive delays or downtime, missed deadlines and customer commitments, and wasted labor. The problem has been solved by the use of barcode labels or using manual serial numbers and spreadsheets; however, these require manual labor. The RFID tag may be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own). Equipment tracking systems may offer advantages, no line of sight required, read Multiple RFID objects at once, scan at a distance, and flexibility. Equipment tracking systems, RFID can be integrated into the embodiments in a variety of manners.

Quantum computing refers to any computational device or method which utilizes properties of quantum states defined by quantum mechanics such as superposition, entanglement, etc. to perform computations. These devices utilize qubits which are the quantum equivalent to bits in a classical computing system, comprised of at least two quantum states or probable outcomes. These outcomes, combined with a coefficient representing the probability of each outcome, describes the possible states, or bits of data, which can be represented by the qubits according to the principle of quantum superposition. These states may be manipulated which may shift the probability of each outcome or additionally add additional possible outcomes to perform a calculation, the final state of which can be measured to achieve the result.

Quantum computing provides significant benefits in the areas of encryption and the simulation of natural systems. Encryption is aided by the uncertain nature of quantum computing in that data is represented by an indeterminate state of probable outcomes, therefore making decryption virtually impossible. The simulation of natural systems, such as chemical and biological interactions, benefit from the fact that nature of quantum computing is the same as the systems being simulated. In medical fields, quantum computing shows the greatest promise for drug discovery and simulating the interaction of drugs with biologic systems, however the same technology might be used to predict the interaction of a biologic system with an implanted device, preventing rejection of an implant by a patient's body, long term function of an implant, and potentially the reaction of a patient to a surgical procedure during a simulation before a procedure or actively during a procedure.

DESCRIPTIONS OF THE DRAWINGS

FIG. 1: Illustrates a system for monitoring a subject, according to an embodiment.

Figure 2:
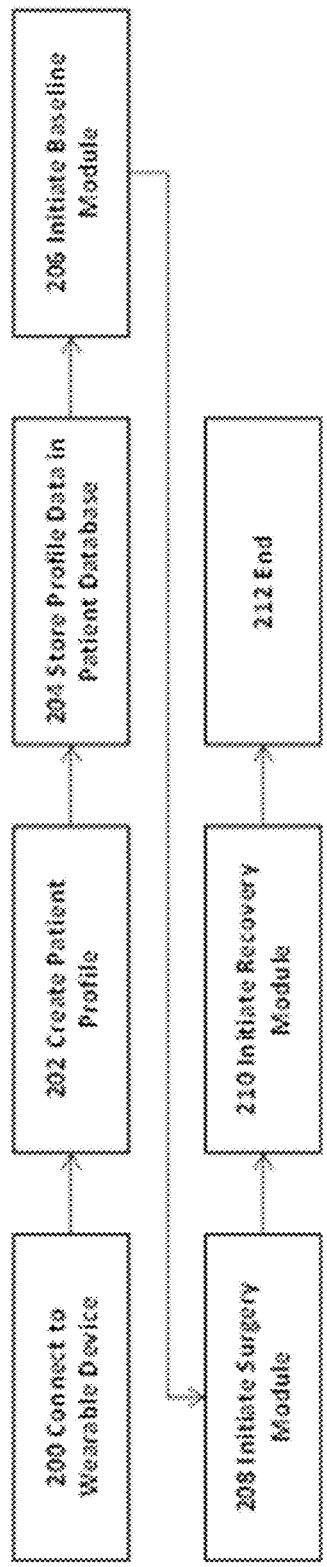

FIG. 2: Illustrates a Base Module, according to an embodiment.

Figure 3:
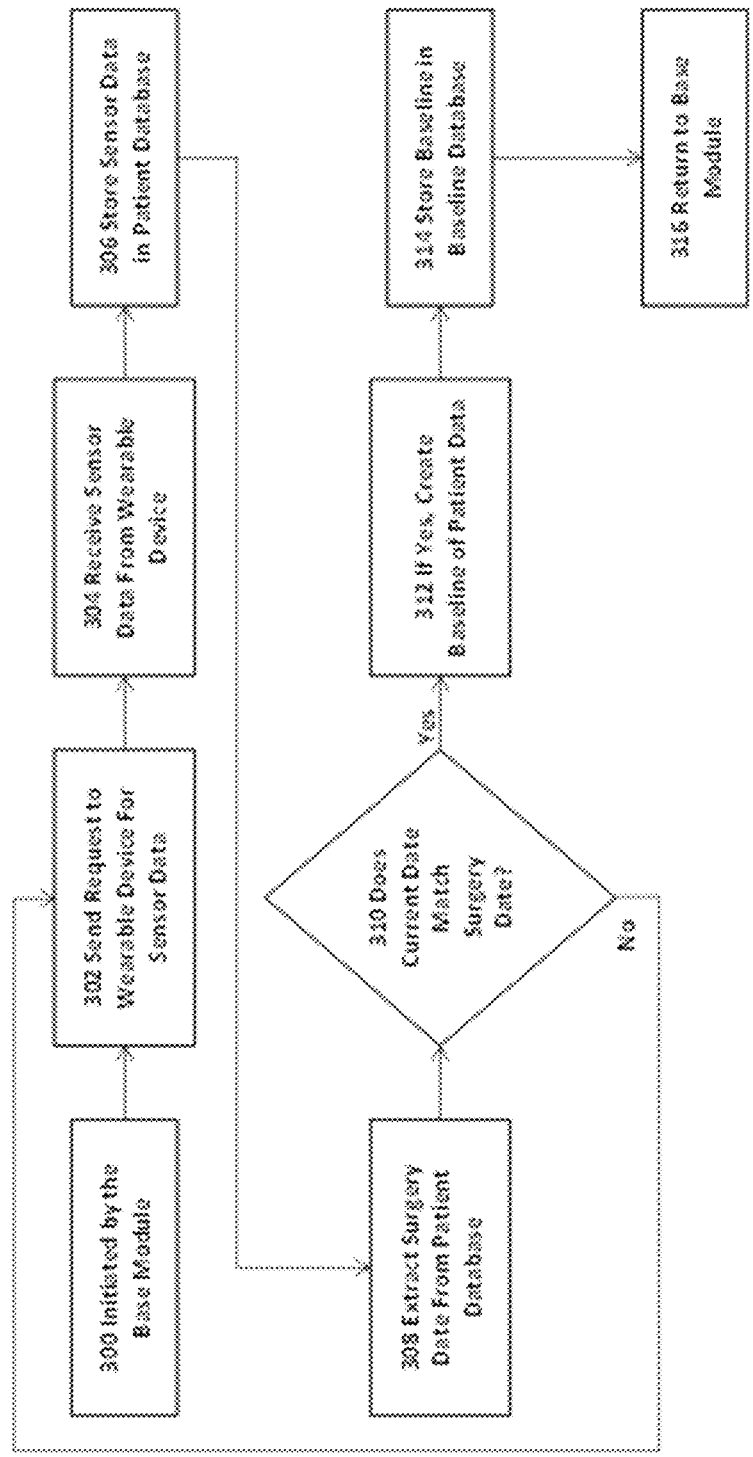

FIG. 3: Illustrates a Baseline Module, according to an embodiment.

Figure 4:
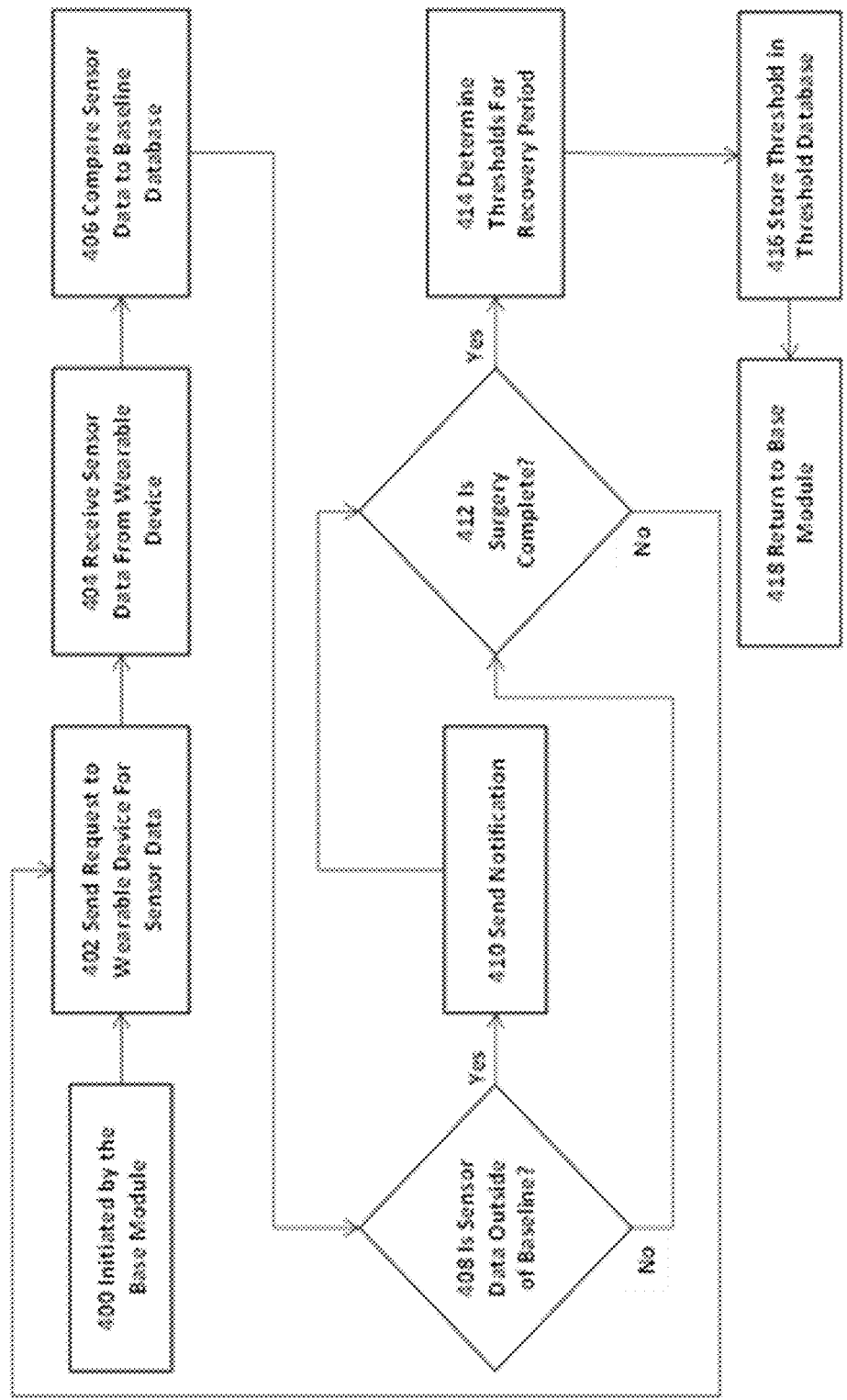

FIG. 4: Illustrates a Surgery Module, according to an embodiment.

Figure 5:
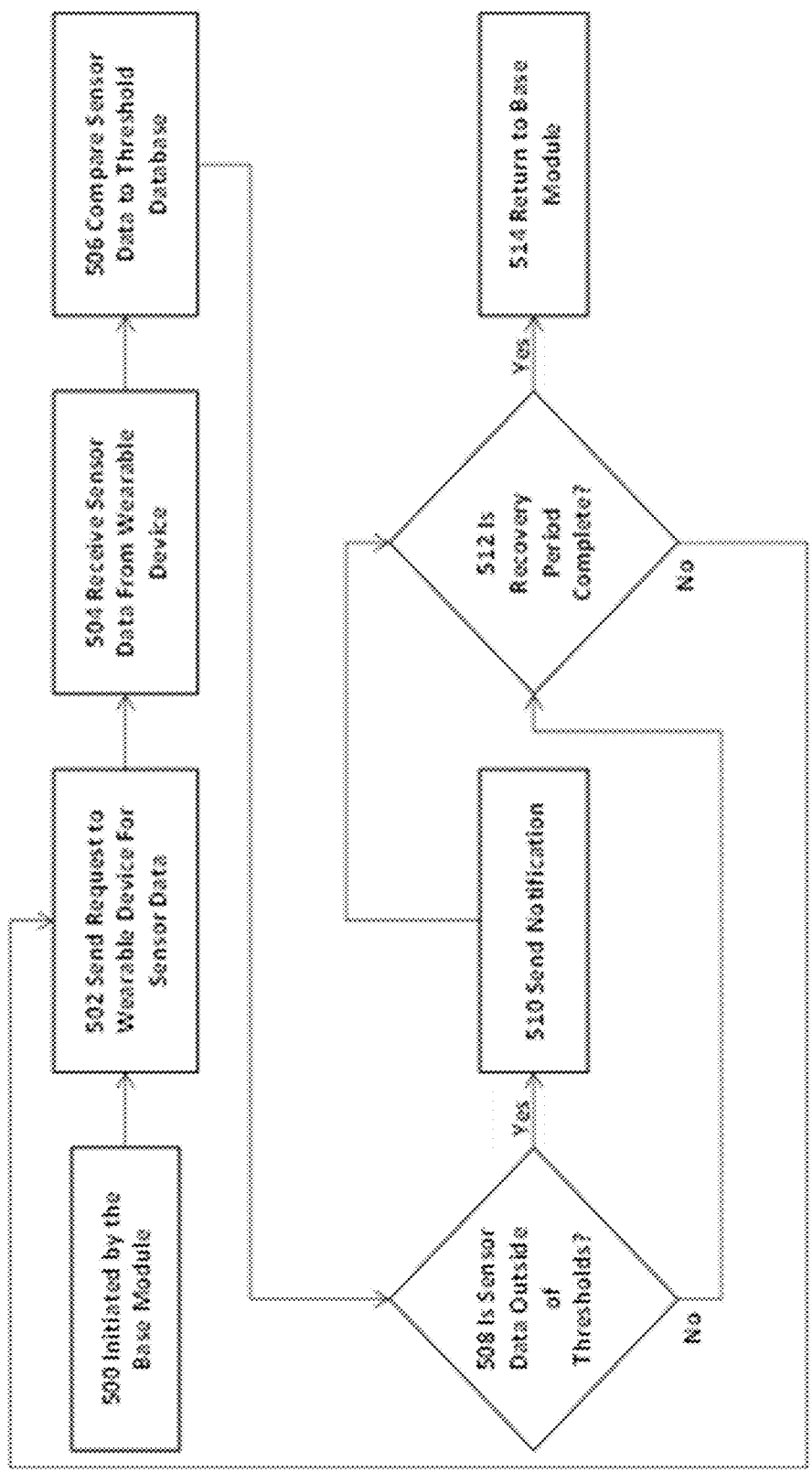

FIG. 5: Illustrates a Recovery Module, according to an embodiment.

Figure 6:
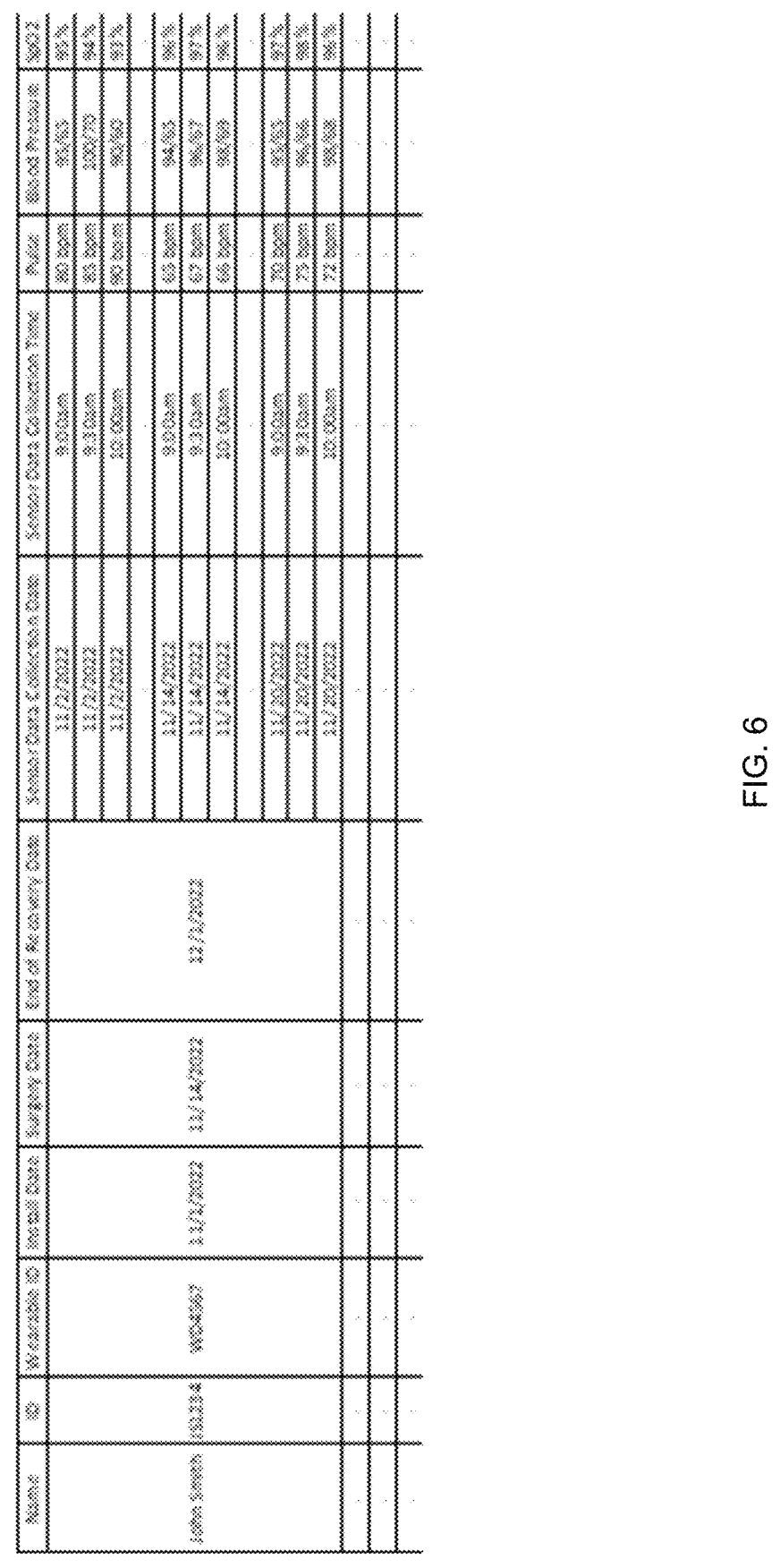

FIG. 6: Illustrates a Patient Database, according to an embodiment.

FIG. 7: Illustrates a Baseline Database, according to an embodiment.

FIG. 8: Illustrates a Threshold Database, according to an embodiment.

Figure 9:
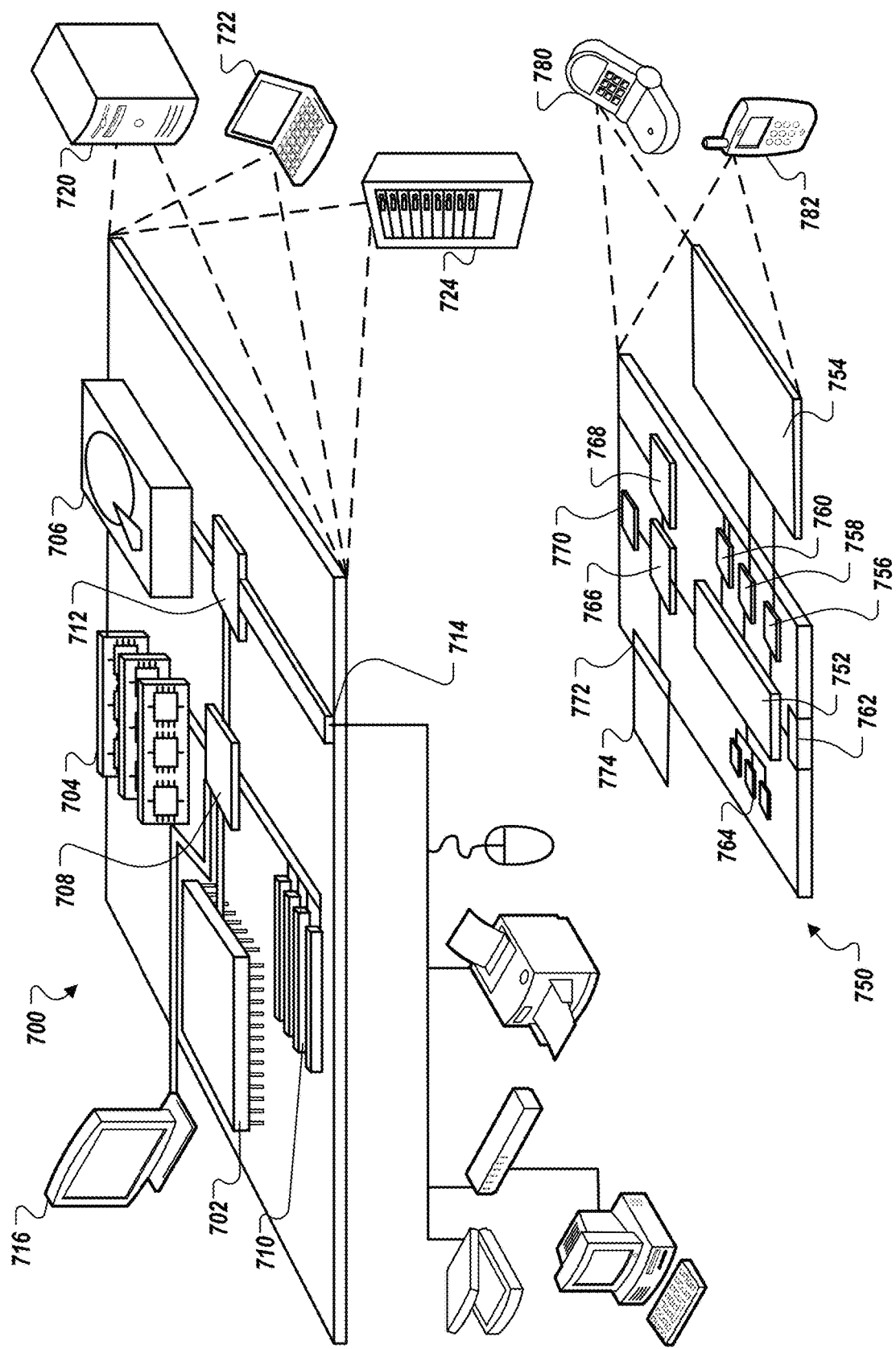

FIG. 9 illustrates a block diagram of computing devices that may be used to implement the systems and methods described in this document, as either a client or as a server or plurality of servers.

DETAILED DESCRIPTION

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

FIG. 1 illustrates a system 100 for monitoring a subject 105. The system 100 includes a surgical robot 102, a wearable device 140, a surgical robot network 124, one or more imaging sources 118, one or more light sources 120, and a cloud 122. Each of the surgical robot 102, the wearable device 140, the surgical robot network 124, one or more imaging sources 118, one or more light sources 120, and the cloud 122 are communicably connected (e.g., via wired or wireless connection) such that data collected can be shared and instructions can be sent throughout the system 100. The system 100 can be configured to collect data from one or more subjects 105, as will be described in further detail below.

The system 100 includes a surgical robot 102 which is a robotic system designed to assist a surgeon in performing a surgical operation on a patient. A surgical robot 102 may include a controller 104, memory 106, and at least one robotic arm 112 with an end effector 114. The surgical robot 102 may further include a user interface 110 for accepting control inputs from a user, such as a surgeon or other medical professional and a communications interface 108 for transmitting and receiving data to and from a cloud 122 for the purpose of training an artificial intelligence operating within the surgical robot or receiving remote commands from a remote user or an artificial intelligence existing external to the surgical robot 102. The surgical robot 102 may additionally comprise a plurality of sensors 116 for providing feedback to the user or an artificial intelligence. In some embodiments, the surgical robot 102 may receive patient sensor 152 data from the wearable device 140 during a surgical procedure to inform a medical professional of the patient's current state by displaying the data on the user interface 110.

Embodiments may include a controller 104 which is a computing device comprised of a processor for performing computations and communicates with a memory 106 for storing data. The controller 104 is in communication with a communications interface 108 and may further be allowed to control the at least one robotic arm 112 and end effector 114 of a surgical robot 102. The controller may be a commercially available central processing unit (CPU) or graphical processing unit (GPU) or may be a proprietary, purpose-build design. More than one controller 104 may operate in tandem and may be of different types, such as a CPU and a GPU. A GPU is not restricted to only processing graphics or image data and may be used for other computations.

Embodiments may include a memory 106 which is the electronic circuitry within a computing device that temporarily stores data for usage by the controller 104. The memory 106 may additionally comprise persistent data storage for storing data used by the controller 104. The memory 106 may be integrated into a controller 104 or may be a discrete component. The memory 106 may be integrated into a circuit, such as soldered on component of a single board computer (SBC) or may a removable component such as a discrete dynamic random-access memory (DRAM) stick, secure digital (SD) card, flash drive, solid state drive (SSD), magnetic hard disk drive (SSD), etc. In some embodiments, memory 106 may be part of a controller 104. Multiple types of memory 106 may be used by the surgical robot 102.

Embodiments may include a communications interface 108 which facilitates communication between the surgical robot 102 and external devices and may comprise a wireless antenna and transceiver or a port for receiving a cable to facilitate a wired connection. Examples of a wired connection include ethernet, universal serial bus (USB) or a proprietary connection. A wireless communications interface 108 may include any of Wi-Fi, Bluetooth, near field communications (NFC) or a cellular communications interface such as 3G, 4G, LTE, or 5G. The communications interface 108 may connect a user interface 110 to the surgical robot 102 or may facilitate access to a local network or a cloud 122 network to access a remote server and/or database.

Embodiments may include a user interface 110 that facilitates interacting with a surgical robot 102 and may include any of a keyboard, computer mouse, trackball, joystick, wireless or wired gamepad, sliders, scroll wheels, touch screen or microphone for receiving voice commands. The user interface 110 may additionally comprise any method of interaction of a user with a surgical robot 102 not listed. The user interface 110 may accept direct inputs, such as from a joystick controlling the movement of a robotic arm or indirect inputs such as commands entered on a keyboard or touch screen such as adjusting the sensitivity of a joystick control or the speed of a robotic arm's 112 movement in response to a joystick. The user interface 110 may also comprise a screen for presenting information to the user such as patient status, imaging data, and navigation data and speakers for providing auditory feedback. The user interface 110 may also utilize haptics to provide feedback to the user. In some embodiments, the user interface 110 may comprise an augmented reality (AR) or virtual reality (VR) headset to enable a surgeon to view imagery from at least one imaging device 118 in real-time and may additionally comprise an overlay, such as highlighting the blood vessels comprising a path which the catheter must be advanced to access the treatment site, such as a blood clot. The user interface 110 may additionally comprise voice or eye tracking controls.

Embodiments may include a robotic arm 112 which is a mechanically actuated arm or lever with at least two degrees of freedom. A robotic arm 112 can include at least one end effector 114 or an imaging device 118 and may include both an end effector 114 and an imaging device 118. The robotic arm 112 may additionally be capable of changing the end effector 114 to facilitate multiple functions and operation of a variety of tools. The robotic arm 114 may be manually controlled or operated in an autonomous or semi-autonomous mode. A surgical robot 102 may have one robotic arm 112 or multiple robotic arms 112, each of which may be operated independently by one or more users or autonomous systems or a combination of users and autonomous systems. Further, embodiments may include an end effector 114 which is the end of a robotic arm 112 which is conducting work. The end effector 114 can be a tool or device for interacting with a physical object and may be a surgical tool intended for acting upon or within a patient or may be a gripping device for securing a separate surgical tool to a robotic arm 112. The end effector 114 may be permanently affixed to the end of a robotic arm 112 or may be detachable allowing for a system of interchangeable end effectors 114 which may alternatively be selected and swapped by a single robotic arm 112 or multiple robotic arms 112. The end effector 114 may comprise a catheter or other tool for accessing a treatment site within a patient. Similarly, the end effector 114 may relate to a deployable device, such as a stent, prior to deployment in a patient. The end effector 114 may be constructed of materials which intentionally absorb, reflect, or are transparent to X-Rays to facilitate the end effector's 114 visibility when viewed using angiography, fluoroscopy, or other imaging modalities, or alternatively allow the X-Rays to pass through to prevent their interference in images. In some embodiments, the end effector 114 may be made to be selectively transparent to X-Rays such as by changing the profile of the end effector 114 or X-Ray absorbing or reflective components to increase or reduce their visibility to an imaging device 118. Further, embodiments may include a sensor 116 which is a measurement tool for monitoring a characteristic or metric associated with a surgical robot 102, end effector 114 or patient. A sensor 116 may be discrete or part of an array or assembly, such as integrated into a catheter. One or more of the sensors 116 may include an electrophysiologic sensor, a temperature sensor, a thermal gradient sensor, a barometer, an altimeter, an accelerometer, a gyroscope, a humidity sensor, a magnetometer, an inclinometer, an oximeter, a colorimetric monitor, a sweat analyte sensor, a galvanic skin response sensor, an interfacial pressure sensor, a flow sensor, a stretch sensor, a microphone, any combination thereof, etc. The sensors 116 may be integrated into the operation of the surgical robot 102 or may monitor the status of a patient. The data acquired by the sensors 116 may be used to train a machine learning algorithm used by the surgical robot 102 or artificial intelligence to control the surgical robot 102. The sensors 116 may additionally comprise an X-Ray dosimeter to monitor the intensity of X-Rays being emitted toward the patient to prevent excessive doses of radiation. The sensors 116 may be utilized to reduce the intensity of the X-Rays or reduce the duration or increase the interval in which the X-Rays are emitted toward the patient to control the dose throughout a procedure.

Embodiments may include an imaging device 118 which refers to any device capable of collecting data which can be used to create an image, or a representation of a physical structure or phenomena. An imaging device 118 may include any device capable of detecting sound or electromagnetic waves and assembling a visual representation of the detected waves. imaging devices 118 may collect waves from any part of the electromagnetic spectrum or sounds at any range of frequencies, often as a matrix of independently acquired measurements which each representing a pixel of a two or three-dimensional image. These measurements may be taken simultaneously or in series via a scanning process or a combination of methods. Some pixels of an image produced by an imaging device 118 may be interpolated from direct measurements representing adjacent pixels in order to increase the resolution of a generated image. Imaging devices 118 may receive or generate imaging data from a plurality of imagining devices 118. The plurality of imaging devices 118 may include, for example, cameras attached to the robotic arm 112, cameras mounted to the ceiling or other structure above the surgical theater, cameras that may be mounted on a tripod or other independent mounting device, cameras that may be body worn by the surgeon or other surgical staff, cameras that may be incorporated into a wearable device, such as an augmented reality device like Google Glass, Microsoft HoloLens, etc., cameras that may be integrated into an endoscopic, microscopic, laparoscopic, or any camera or other imaging device 118 (e.g. ultrasound) that may be present in the surgical theater. The imaging device 118 may include any algorithm or software module capable of determining qualitative or quantitative data from medical images, which may be, for example, a deep learning algorithm that has been trained on a data set of medical images. An imaging device 118 may further refer to a device used to acquire medical imagery by any means including magnetic resonance imaging (MRI), computed tomography (CT), X-Ray, positron emission tomography (PET), ultrasound, arthrography, angiography, fluoroscopy, myelography, etc. An imaging device 118 may acquire images in real-time or be used to create composite images or models in real-time.

Embodiments may include a light source 120 such as surgical lights also referred to as operating light, refers to an instrument that performs illumination of a local area or cavity of the patient. The light source 120 plays an important role in illumination before, during, and after a medical procedure. The light source 120 may be categorized by lamp type as conventional (incandescent) and LED (light-emitting diode). The light source 120 may be categorized by mounting configuration as ceiling-mounted, wall-mounted, or floor stand. The light source 120 may be categorized by type as tungsten, quartz, and/or xenon halogens and light-emitting diodes (LEDs). The light source 120 may include sterilizable handles which allow the surgeon to adjust light positions. Some factors affecting the light source 120 may be illumination, shadow management (cast shadows and contour shadows), the volume of light, heat management, fail-safe surgical lighting. The light source 120 can be integrated into the embodiments in a variety of manners.

Embodiments may include a cloud 122 which is a distributed network of computers comprising servers and databases. A cloud 122 may be a private cloud 122, where access is restricted by isolating the network such as preventing external access, or by using encryption to limit access to only authorized users. Alternatively, a cloud 122 may be a public cloud 122 where access is widely available via the internet. A public cloud 122 may not be secured or may be include limited security features. Further, embodiments may include a surgical robot network 124 which may be a network connected to the wearable device 140 and the surgical robot 102 in which the surgical robot network 124 may receive and send data to the wearable device 140 and surgical robot 102, provide controls to a user for the surgical robot 102 through a user interface 110, and allow a user to send data to the surgical robot 102 related to a designed, tested, or created surgical process for a patient.

Embodiments may include a base module 126 which connects to the wearable device 140, creates a profile for the patient, stores the patient profile data in the patient database 134, and initiates the baseline module 128, the surgery module 130, and the recovery module 132, and once the patient's recovery period is complete the base module 126 ends.

Embodiments may include a baseline module 128 which begins by being initiated by the base module 126. The baseline module 128 sends a request to the wearable device 140 for the sensor 152 data. The baseline module 128 receives the sensor 152 data from the wearable device 140. The baseline module 128 stores the received sensor 152 data in the wearable device 140. The baseline module 128 extracts the surgery date from the patient database 134. The baseline module 128 determines if the current date matches the extracted surgery date from the patient database 134. If it is determined that the current date does not match the extracted surgery date from the patient database 134 the baseline module 128 returns to sending a request to the wearable device 140 for the sensor 152 data. If it is determined that the current date matches the extracted surgery date from the patient database 134 the baseline module 128 creates a baseline of the patient data stored in the patient database 134. Then the baseline module 128 stores the created baseline from the patient's data in the baseline database 136. The baseline module 128 returns to the base module 126.

Embodiments may include a surgery module 130 which begins by being initiated by the base module 126. The surgery module 130 sends a request to the wearable device 140 for the sensor 152 data. The surgery module 130 receives the sensor 152 data from the wearable device 140. The surgery module 130 compares the received sensor 152 data to the baseline database 136. The surgery module 130 determines if the sensor 152 data is outside of the patient's baseline data stored in the baseline database 136. If it is determined that the sensor 152 data is outside of the patient's baselines stored in the baseline database 136 the surgery module 130 sends a notification to the wearable device 140. If it is determined that the sensor 152 data is not outside the patient's baseline data stored in the baseline database 136 the surgery module 130 determines if the surgery is complete. If it is determined that the surgery is not complete the surgery module 130 returns to sending a request for the sensor 152 data to the wearable device 140. If it is determined that the surgery is complete the surgery module 130 determines the thresholds for the patient's recovery period. The surgery module 130 stores the thresholds in the threshold database 138. The surgery module 130 returns to the base module 126.

Embodiments may include a recovery module 132 which begins by being initiated by the base module 126. The recovery module 132 sends a request to the wearable device 140 for the sensor 152 data. The recovery module 132 receives the sensor 152 data from the wearable device 140. The recovery module 132 compares the sensor 152 data to the threshold database 138. The recovery module 132 determines if the received sensor 152 data is outside of the thresholds stored in the threshold database 138. If it is determined that the received sensor 152 data is outside of the thresholds stored in the threshold database 138 the recovery module 132 can initiate various actions. For example, the recovery module 132 can send a notification to the wearable device 140. In some embodiments, the recovery module 132, responsive to the determination that the received sensor 152 data is outside of the thresholds stored in the threshold database 138, can initiate medical interventions, therapies, and/or treatment steps that are automated by the system 100. For example, the recovery module 132 can control the output of an insulin pump, can include intra-operative automation such as utilizing the threshold to update the anesthesiology system to control sedation. In some embodiments, the recovery module 132, responsive to the determination that the received sensor 152 data is outside of the thresholds stored in the threshold database 138, can initiate collecting additional data from a secondary sensor (e.g., heart rate thresholds being crossed may initiate data collection from an SpO2 sensor), and the secondary sensor data can be analyzed with respect to a baseline collected preoperatively. In some embodiments, responsive to the determination that the received sensor 152 data is outside of the thresholds stored in the threshold database 138, the recovery module 132 can initiate control or modulation of the robotic surgical device 102 (e.g., the sensor threshold being crossed can cause the robot 102 to pause or delay a task until an anesthesiology task has been completed.) If it is determined that the received sensor 152 data is not outside of the thresholds stored in the threshold database 138 the recovery module 132 determines if the patient's recovery period is complete. If it is determined that the recovery period is not complete the process returns to sending a request to the wearable device 140 for the sensor 152 data. If it is determined that the patient's recovery period is complete the recovery module 130 returns to the base module 126.

Embodiments may include a patient database 134 which is created through the process described in the base module 126 in which the patient's profile data is stored and through the processes described in the baseline module 128, the surgery module 130, and the recovery module 132 in which the patient's sensor 152 data is collected and stored to either create a baseline for surgery or threshold for recovery as well as compared to the baseline database 136 and threshold database 138 to determine if any notifications or actions are required during the surgical procedure or recovery period. The database may contain the patient's name, a patient ID or unique identifier, a wearable ID, the install date or the date the patient began wearing the wearable device 140, the surgery date or the date the patient will have the surgical procedure, the end of recovery date or the date the patient's recovery period will end and thus no longer will be wearing the wearable device 140, the sensor 152 data collection date or the date the sensor 152 data was collected, the sensor 152 data collection time or the time in which the sensor data was collected, the patient's pulse rate or heart rate such as beats per minute (bpm), the patient's blood pressure, and the patient's blood oxygen saturation levels or SpO2 levels. In some embodiments, the sensor 152 data may be collected at certain points during the day or randomly collected during the day. In some embodiments, the sensor 152 data may be continuously collected by the surgical robot network 124. In some embodiments, the sensor 152 data may include data from temperature sensors, blood glucose sensors, heart rate sensors, range of motion assessment sensors, electromyography (EMG) sensors, pedometer sensors, etc. In some embodiments, the sensor 152 data may track patient data related to their surgical procedure, for example if a patient is having a disc replacement surgery the sensor 152 data may track the patient's daily movements before and after the surgery to determine if the patient is improving their mobility. For example, if the patient has stent implanted to open a clogged artery the sensor 152 data may collect the patient's heart rate, such as resting heart rate, before and after the procedure to determine if the patient's recovery is going as planned. In some embodiments, the medical professionals overseeing the patient's care may be able to view and analyze the patient's sensor 152 data to determine if the medications the patient is using for recovery are helping or if they are the underlying cause of certain sensor 152 readings. In some embodiments, the sensor 152 data may be used to detect early warning signs of potential serious conditions post-surgery, such as performing physical therapy too intensely, help reminder patients of post-surgical care routines, such as medications, exercise, nutrition, hydration, wound cleaning, etc., monitor medication reactions, etc.

Embodiments may include a baseline database 136 which is created in the process described in the baseline module 128 in which a baseline is created using the patient's sensor 152 data that is stored in the patient database 134 to be used during the patient's surgical procedure to determine if any of the patient's sensor 152 data goes over or below the created baseline. The database contains the patient's name, the patient's ID or unique identifier, and the patient's baseline sensor 152 readings, such as a high pulse, low pulse, high blood pressure, low blood pressure, high SpO2, low SpO2, in which if the sensor 152 goes above the high baseline or below the low baseline, a notification is sent. In some embodiments, the wearable device 140 may receive the notification. In some embodiments, the surgical robot network 124 may send the notification to the surgical robot 102 user interface 110 to inform the medical professionals. In some embodiments, the sensor 152 data received from the wearable device 140 may be sent to the surgical robot 102 user interface 110 to inform the medical professional of certain patient health parameters or medical information. In some embodiments, the baseline database 136 may include recommendation actions that a medical professional should take to return the patient's sensor 152 data back to the baseline readings. In some embodiments, the baseline database 136 may initiate (e.g., by the surgical robot 102) automated innervations, treatment steps, and/or other actions to return the patient's sensor 152 data back to the baseline readings. In some embodiments, the patient's vitals may be taken by the wearable device 140 and sent to the surgical robot 102. In some embodiments, the baseline database 136 may be able to determine certain medical complications if the patient's health data falls into a certain range, such as a huge drop in blood pressure may be caused by a bleeding event that needs to be stopped immediately, if the patient is about to go into shock due to a severe drop in blood pressure from blood loss and the blood loss needs to be stopped immediately, etc. In some embodiments, the baseline database 136 can initiate interventions, or send instructions throughout the system 100 to initiate interventions to automatically mitigate the medical complications. For example, the baseline database 136 can initiate a stop procedure step that stops the automated operations from occurring (e.g., at the surgical robot 102) until the patient's health data stabilizes within the thresholds. In some embodiments, the system 100 can initiate an intervention to stabilize the patient's health data (e.g., surgical robot 102 and end effectors 114 can clamp artery in response to pressure drop). In some embodiments, an abnormal threshold cross of the sensor data can initiate an automated stop procedure, an automated modification of anesthesia, automated administering medication, and other automated surgical interventions. In some embodiments, the database may be updated depending on the stages of surgery, such as the surgical robot 102 sending data back to the surgical robot network 124 and the patient's baselines change depending on whether they are being administered anesthesia, are being prepped for surgery, are undergoing the procedure, such as the first incision, implanting a stent, suturing the incision, etc., coming off the anesthesia, immediate recovery from the surgery, such as the first hour or two after the surgery is completed, etc.

Embodiments may include a threshold database 138 which is created during the process described in the surgery module 130 in which the thresholds may be created by a medical professional inputting the thresholds in the surgical robot 102 user interface 110 and sent to the surgical robot network 124 to be used during the patient's recovery period. The database contains the patient's name, the patient's ID or unique identifier, and the patient's threshold sensor 152 readings, such as a high pulse, low pulse, high blood pressure, low blood pressure, high SpO2, low SpO2, in which if the sensor 152 goes above the high threshold or below the low threshold, a notification is sent. The thresholds may be used to assist in the patient's recovery process to ensure the patient is recovery properly, performing the post-surgery tasks, such as performing exercise, taking the prescribed medication, etc. The patient's recovery period sensor 152 data may be analyzed by a medical professional to detect any anomalies or potential complications for the patient. In some embodiments, the wearable device 140 may receive the notification. In some embodiments, the surgical robot network 124 may send the notification to the medical professional to inform the medical professionals. In some embodiments, the threshold database 138 may include recommendation actions that a medical professional should take to return the patient's sensor 152 data back to in-between the thresholds. In some embodiments, the threshold database 138 may be able to determine certain medical complications if the patient's health data falls into a certain range, such as pneumonia, blood clots, deep vein thrombosis, which may lead to heart attacks, strokes, embolisms, etc., pulmonary complications, etc. In some embodiments, the database may be updated depending on the stages of recovery, such as directly after the surgery has been completed, the bed rest period in which the patient remains in the hospital post-surgery, when the patient is first sent home, when the patient may be allowed to perform normal daily activities, etc.

Embodiments may include a wearable device 140 which is a device that is autonomous, noninvasive and that performs a specific medical function such as monitoring or support over a prolonged period of time. The term wearable implies that the device is either supported by the human body or clothing. The wearable device 140 may be worn as accessories, embedded in clothing, implanted in the user's body, or even tattooed on the skin. The devices may be hands-free gadgets with practical uses, powered by microprocessors and enhanced with the ability to send and receive data via the cloud 122 or Internet. The wearable device 140 may monitor patient data through a plurality of sensors 152 to be used to create a baseline of patient data prior to an operation, during an operation, and create thresholds to improve the patient's recovery during the post operation recovery period.

Embodiments may include an operating system 142 that may be a system software that manages computer hardware, software resources, and provides common services for computer programs. Time-sharing operating systems schedule tasks for efficient use of the system and may also include accounting software for cost allocation of processor time, mass storage, printing, and other resources. For hardware functions such as input and output and memory allocation, the operating system 142 acts as an intermediary between programs and the computer hardware, although the application code is usually executed directly by the hardware and frequently makes system calls to an OS function or is interrupted by it.

Embodiments may include a memory 144 which may include, but is not limited to, fixed (hard) drives, magnetic tape, floppy diskettes, optical disks, Compact Disc Read-Only Memories (CD-ROMs), and magneto-optical disks, semiconductor memories, such as ROMs, Random Access Memories (RAMs), Programmable Read-Only Memories (PROMs), Erasable PROMs (EPROMs), Electrically Erasable PROMs (EEPROMs), flash memory, magnetic or optical cards, or other type of media/machine-readable medium suitable for storing electronic instructions. The memory 144 may comprise modules implemented as a program.

Embodiments may include a controller 146 for performing computations and communicates with a memory 144 for storing data. The controller 146 is in communication with a communications interface 156. The controller 146 may be a commercially available central processing unit (CPU) or graphical processing unit (GPU) or may be a proprietary, purpose-build design. More than one controller 146 may operate in tandem and may be of different types, such as a CPU and a GPU. A GPU is not restricted to only processing graphics or image data and may be used for other computations.

Embodiments may include a processor 148 may be configured to decode and execute any instructions received from one or more other electronic devices or server(s). The processor 148 may include one or more general-purpose processors (e.g., INTEL® or Advanced Micro Devices® (AMD) microprocessors) and/or one or more special purpose processors (e.g., digital signal processors or Xilinx® System On Chip (SOC) Field Programmable Gate Array (FPGA) processor). The processor 148 may be configured to execute one or more computer-readable program instructions, such as program instructions to carry out any of the functions described in this description.

Embodiments may include a user interface(s) 150 which may either accept inputs from users or provide outputs to the users, or may perform both the actions. In one case, a user can interact with the user interface(s) 150 using one or more user-interactive objects and devices. The user-interactive objects and devices may comprise user input buttons, switches, knobs, levers, keys, trackballs, touchpads, cameras, microphones, motion sensors, heat sensors, inertial sensors, touch sensors, or a combination of the above. Further, the user interface(s) 150 may either be implemented as a Command Line Interface (CLI), a Graphical User Interface (GUI), a voice interface, or a web-based user-interface.

Embodiments may include a plurality of sensors 152 which may collect data from a patient using the wearable device 140 prior, during, and after a surgical procedure. The sensors 152 may include a temperature sensor, a pulse sensor, blood pressure sensor, blood oxygen saturation sensor, blood glucose sensors, heart rate sensors, range of motion assessment sensors, electromyography (EMG) sensors, pedometer sensors, etc. The sensors 152 may collect and send the data to the surgical robot network 124 to be used to monitor a patient's health condition or health parameters prior to, during, and after a surgical procedure. In some embodiments, the sensors 152 may include an accelerometer, gyroscopes, magnetometers, global positioning system (GPS), pressure sensors, etc.

Embodiments may include a power source 154 which may be an electrical device that supplies electric power to an electrical load. The main purpose of a power source 154 is to convert electric current from a source to the correct voltage, current, and frequency to power the load. The power source 154 may be a battery, wireless charging battery, solar charging battery, kinetically charged battery, etc.

Embodiments may include a communications interface 156 which allows the wearable device 140 to communicate with external devices and may comprise a wireless antenna and transceiver or a port for receiving a cable to facilitate a wired connection. Examples of a wired connection include ethernet, universal serial bus (USB) or a proprietary connection. A wireless communications interface 156 may include any of Wi-Fi, Bluetooth, near field communications (NFC) or a cellular communications interface such as 3G, 4G, LTE, or 5G. The communications interface 156 may connect a user interface 150 to the wearable device 156 or may facilitate access to a local network or a cloud 122 network to access a remote server and/or database.

Functioning of the base module 126 will now be explained with reference to FIG. 2. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

This figure displays the base module 126. The process begins with the base module 126 connecting, at step 200, to the wearable device 140. For example, the base module 126 may connect to the wearable device 140 through the cloud 122 to the communication interface 156 to receive data from the wearable device 140. In some embodiments, the base module 126 may also connect to the surgical robot 102 to send data from the wearable device 140 to the surgical robot 102 and vice versa. In some embodiments, a medical professional may input data to the surgical robot network 124, such as surgical procedures, patient options, baseline sensor 52 data, sensor 152 thresholds, etc., that may be stored on the surgical robot network 124 or sent to the wearable device 140 or surgical robot 102. The base module 126 creates, at step 202, the patient's profile. For example, the patient or medical professional may input the patient's profile information, such as the patient's name, address, medical insurance, required surgical procedure, etc. In some embodiments, the patient's profile may contain the baseline information for the surgery as well as the threshold data for the recovery period. In some embodiments, the baseline information and threshold data may be updated based on the received patient data from the wearable device 140. In some embodiments, the data may be continuously collected and stored in the patient database 134 during the entire process including prior, during and after surgery. The base module 126 stores, at step 204, the patient's profile data in the patient database 134. For example, the base module 126 stores the patient's profile data, such as the patient's profile information, such as the patient's name, address, medical insurance, required surgical procedure, etc. The base module 126 initiates, at step 206, the baseline module 128. For example, the baseline module 128 begins by being initiated by the base module 126. The baseline module 128 sends a request to the wearable device 140 for the sensor 152 data. The baseline module 128 receives the sensor 152 data from the wearable device 140. The baseline module 128 stores the received sensor 152 data in the wearable device 140. The baseline module 128 extracts the surgery date from the patient database 134. The baseline module 128 determines if the current date matches the extracted surgery date from the patient database 134. If it is determined that the current date does not match the extracted surgery date from the patient database 134 the baseline module 128 returns to sending a request to the wearable device 140 for the sensor 152 data. If it is determined that the current date matches the extracted surgery date from the patient database 134 the baseline module 128 creates a baseline of the patient data stored in the patient database 134. The baseline of the patient data or the baseline data set can be automatically segmented from the other data sets such as the background data acquired from the wearable device 140 before the baseline time period. The automatic segmentation of the baseline data from the background data (or other data sets such as future surgery data set, future recovery data sets) facilitates increased processing speed, reduced processing load on the system, increases processing efficiency, saves memory in the system, among other benefits. The automatic segmentation of the data can advantageously facilitate improvements to the processing efficiency, memory savings, etc. within the system to ensure a seamless transition into collection of the baseline data set and reduce or eliminate processing delays that could occur without the automatic segmentation of the baseline data set. Then the baseline module 128 stores the created baseline from the patient's data in the baseline database 136. The baseline module 128 returns to the base module 126. The base module 126 initiates, at step 208, the surgery module 130. For example, the surgery module 130 begins by being initiated by the base module 126. The surgery module 130 sends a request to the wearable device 140 for the sensor 152 data. The surgery module 130 receives the sensor 152 data from the wearable device 140. The surgery module 130 compares the received sensor 152 data to the baseline database 136. The surgery module 130 determines if the sensor 152 data is outside of the patient's baseline data stored in the baseline database 136. If it is determined that the sensor 152 data is outside of the patient's baselines stored in the baseline database 136 the surgery module 130 sends a notification to the wearable device 140. If it is determined that the sensor 152 data is not outside the patient's baseline data stored in the baseline database 136 the surgery module 130 determines if the surgery is complete. If it is determined that the surgery is not complete the surgery module 130 returns to sending a request for the sensor 152 data to the wearable device 140. If it is determined that the surgery is complete, the surgery module 130 determines the thresholds for the patient's recovery period. For example, the thresholds are created by comparing the baseline thresholds to the procedure thresholds, and determining a recovery threshold based on the comparison. The thresholds can be created by setting an expected values based on how the surgery went, the patient's age, the type of procedure, etc. A risk assessment of the patient can impact the patient's recovery period (e.g., certain conditions may include a reduced or increased risk post-surgery that can impact the recovery time). Additional patient metrics and outcomes can impact the recovery threshold(s) such as internal bleeding, infection, blood pressure, heart rate, and correlated to age, weight/height, gender, as well as the baseline data. Recovery period can be dynamically adjusted post-surgery based on sensor data coherence or divergence from a baseline. For example, the patient may be recovering slower or faster than expected based on their wearable data, and the recovery threshold could update in real time based on the sensor data. The surgery module 130 stores the thresholds in the threshold database 138. The surgery module 130 returns to the base module 126. The base module 126 initiates, at step 210, the recovery module 132. For example, the recovery module 132 begins by being initiated by the base module 126. The recovery module 132 sends a request to the wearable device 140 for the sensor 152 data. The recovery module 132 receives the sensor 152 data from the wearable device 140. The recovery module 132 compares the sensor 152 data to the threshold database 138. The recovery module 132 determines if the received sensor 152 data is outside of the thresholds stored in the threshold database 138. If it is determined that the received sensor 152 data is outside of the thresholds stored in the threshold database 138 the recovery module 132 sends a notification to the wearable device 140, initiates automated interventions and/or treatment steps by the system 100 including the surgical robot 102. If it is determined that the received sensor 152 data is not outside of the thresholds stored in the threshold database 138 the recovery module 132 determines if the patient's recovery period is complete. If it is determined that the recovery period is not complete the process returns to sending a request to the wearable device 140 for the sensor 152 data. If it is determined that the patient's recovery period is complete the recovery module 130 returns to the base module 126. The base module 126 ends, at step 212. For example, once the recovery period for the patient is complete the base module 126 ends the process of collecting and monitoring the patient data from the wearable device 140. In some embodiments, if the patient requires an additional surgery, extended recovery period, additional monitoring due to a medication adjustment, the process may return to the baseline module 128, the surgery module 130, and/or the recovery module 132.

Functioning of the baseline module 128 will now be explained with reference to FIG. 3. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

This figure displays the baseline module 128. The process begins with the baseline module 128 being initiated, at step 300, by the base module 126. The baseline module 128 sends, at step 302, a request to the wearable device 140 for the sensor 152 data. For example, the baseline module 128 sends a request to the wearable device 140 for the sensor 152 data, such as the patient's pulse rate or heart rate such as beats per minute (bpm), the patient's blood pressure, and the patient's blood oxygen saturation levels or SpO2 levels. In some embodiments, the sensor 152 data may be collected at certain points during the day or randomly collected during the day. In some embodiments, the sensor 152 data may be continuously collected by the surgical robot network 124. In some embodiments, the sensor 152 data may include data from temperature sensors, blood glucose sensors, heart rate sensors, range of motion assessment sensors, electromyography (EMG) sensors, pedometer sensors, etc. The baseline module 128 receives, at step 304, the sensor 152 data from the wearable device 140. For example, the baseline module 128 receives the sensor 152 data from the wearable device 140. In some embodiments, the sensors 152 that are used by the wearable device 140 or sent by the wearable device 140 may be directly related to the surgical procedure that will be performed on the patient that may be a concern for the medical professionals, such as heart rate if the patient is having a stent implanted, the patient's mobility or movement if the patient is having back surgery, etc. The baseline module 128 stores, at step 306, the received sensor 152 data from the wearable device 140 in the patient database 134. For example, the baseline module 128 stores the sensor 152 data in the patient database 134, such as the patient's pulse rate or heart rate such as beats per minute (bpm), the patient's blood pressure, and the patient's blood oxygen saturation levels or SpO2 levels. In some embodiments, the sensor 152 data may be collected at certain points during the day or randomly collected during the day. In some embodiments, the sensor 152 data may be continuously collected by the surgical robot network 124. In some embodiments, the sensor 152 data may include data from temperature sensors, blood glucose sensors, heart rate sensors, range of motion assessment sensors, electromyography (EMG) sensors, pedometer sensors, etc. In some embodiments, the sensor 152 data may be continuously received and stored in the patient database 134 throughout the course of the patient's pre-surgery process, surgical process, and post-surgery process. The baseline module 128 extracts, at step 308, the surgery date from the patient database 134. For example, the baseline module 128 may extract the surgery data from the patient database 134, such as 11/14/2022 and compare the date to the current date to determine if the patient is still in the pre-surgery process. In some embodiments, the wearable device 140 may inform the baseline module 128 that the pre-surgery process is completed, and the surgery process is beginning, and the wearable device 140 may send a signal to the baseline module 128 to create the baselines for the patient or to send a notification to the medical professional to create the baselines for the patient based on the collected sensor 152 data during the pre-surgery process. In some embodiments, the pre-surgery process may be the time prior to the patient's surgical procedure, such as hours, days, weeks, etc., to create an appropriate baseline of sensor 152 data. The baseline module 128 determines, at step 310, if the current date matches the extracted surgery date from the patient database 134. If it is determined that the current date does not match the extracted surgery date from the patient database 134 the baseline module 128 returns to sending a request to the wearable device 140 for the sensor 152 data. For example, if the patient is still in the pre-surgery process the process will continue to collect the patient's data from the sensors 152 located in the wearable device 140. If it is determined that the current date matches the extracted surgery date from the patient database 134 the baseline module 128 creates, at step 312, a baseline of the patient data stored in the patient database 134. For example, the medical professional may analyze the patient's sensor 152 data during the pre-surgery process and create a baseline of what the sensor 152 data should be during the surgical procedure. The medical professional may input the baselines in the surgical robot network 124. In some embodiments, the baselines may be created through determining the averages of the patient's sensor 152 data throughout the pre-surgery process. In some embodiments, the baselines may be created through determining the patient's low and high sensor 152 readings throughout the pre-surgery process. In some embodiments, the baselines may be created through comparing the patient's entire profile to historical profiles to find similar patient's and extract the historical patient's baselines. For example, the historical database may be filtered for patients with the same age, conditions, surgical procedure, location, ethnicity, sex, etc. and determine the closest match or closest matches to current patient to use the historical baselines for the current patient. Then the baseline module 128 stores, at step 314, the created baseline from the patient's data in the baseline database 136. For example, the baseline module 128 stores the baselines in the baseline database 136, such as a high pulse, low pulse, high blood pressure, low blood pressure, high SpO2, low SpO2, in which if the sensor 152 goes above the high baseline or below the low baseline, a notification is sent. In some embodiments, the baseline data may include data from temperature sensors, blood glucose sensors, heart rate sensors, range of motion assessment sensors, electromyography (EMG) sensors, pedometer sensors, etc. The baseline module 128 returns, at step 316, to the base module 126.

Functioning of the surgery module 130 will now be explained with reference to FIG. 4. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

This figure displays the surgery module 130. The process begins with the surgery module 130 being initiated, at step 400, by the base module 126. In some embodiments, the surgery module 130 may be initiated by a medical professional when the patient arrives to the medical facility for the medical procedure to track the patient's sensor 152 data just before the surgery, during the surgery and immediately after the surgery. For example, the patient's data may be monitored prior to the anesthesia being administered, when the anesthesia is administered, when the patient arrives in operating room, while the operation is being performed, immediately following the operation, and while the anesthesia is wearing off, etc. The surgery module 130 sends, at step 402, a request to the wearable device 140 for the sensor 152 data. For example, the surgery module 130 sends a request to the wearable device 140 for the sensor 152 data, such as the patient's pulse rate or heart rate such as beats per minute (bpm), the patient's blood pressure, and the patient's blood oxygen saturation levels or SpO2 levels. In some embodiments, the sensor 152 data may be collected at certain points during the day or randomly collected during the day. In some embodiments, the sensor 152 data may be continuously collected by the surgical robot network 124. In some embodiments, the sensor 152 data may include data from temperature sensors, blood glucose sensors, heart rate sensors, range of motion assessment sensors, electromyography (EMG) sensors, pedometer sensors, etc. The surgery module 130 receives, at step 404, the sensor 152 data from the wearable device 140. For example, the surgery module 130 receives the sensor 152 data from the wearable device 140. In some embodiments, the sensors 152 that are used by the wearable device 140 or sent by the wearable device 140 may be directly related to the surgical procedure that will be performed on the patient that may be a concern for the medical professionals, such as heart rate if the patient is having a stent implanted, the patient's mobility or movement if the patient is having back surgery, etc. In some embodiments, the sensors 152 can be selected based on relevance to the underlying condition, nature of the surgery, patient risk factors, among other selection criteria. In some embodiments, the system can implement a primary data type such as a heart rate, blood pressure, or other data types, and there may be related secondary sensors such as skin temperature, SpO2, Heart Rate Variability, galvanic skin response (measure stress), etc. In some embodiments, the surgery module 130 may store the received sensor 152 data in the patient database 134 and compare the data in the patient database 134 to the baseline database 136. The surgery module 130 compares, at step 406, the received sensor 152 data to the baseline database 136. For example, the surgery module 130 compares the patient's received sensor 152 data, such as pulse, blood pressure, oxygen saturation levels, etc. to the baselines stored in the baseline database 136. The comparison allows medical professionals to monitor, track, and react appropriately to the patient's data by receiving a notification if the patient's data is above or below the patient's baseline data. In some embodiments, the sensor 152 data received from the wearable device 140 may be sent to the surgical robot 102 user interface 110 to inform the medical professional of certain patient health parameters or medical information. In some embodiments, the baseline database 136 may include recommendation actions that a medical professional should take to return the patient's sensor 152 data back to the baseline readings. In some embodiments, the patient's vitals may be taken by the wearable device 140 and sent to the surgical robot 102. In some embodiments, the baseline database 136 may be able to determine certain medical complications if the patient's health data falls into a certain range, such as a huge drop in blood pressure may be caused by a bleeding event that needs to be stopped immediately, if the patient is about to go into shock due to a severe drop in blood pressure from blood loss and the blood loss needs to be stopped immediately, etc. In some embodiments, the database may be updated depending on the stages of surgery, such as the surgical robot 102 sending data back to the surgical robot network 124 and the patient's baselines change depending on whether they are being administered anesthesia, are being prepped for surgery, are undergoing the procedure, such as the first incision, implanting a stent, suturing the incision, etc., coming off the anesthesia, immediate recovery from the surgery, such as the first hour or two after the surgery is completed, etc. The surgery module 130 determines, at step 408, if the sensor 152 data is outside of the patient's baseline data stored in the baseline database 136. For example, the surgery module 130 compares the received sensor 152 data to the patient's baseline data stored in the baseline database 136 to determine if the patient's data is outside of the baselines provided and send a notification to the medical professional through the wearable device 140 or the surgical robot 102 user interface 110 to inform the medical professional. If it is determined that the sensor 152 data is outside of the patient's baselines stored in the baseline database 136 the surgery module 130 sends, at step 410, a notification to the wearable device 140. In some embodiments, the surgery module 130 may send a notification to the surgical robot 102 user interface 110 to inform the medical professional performing the procedure that the patient's data is above or below the baselines. In some embodiments, the surgery module 130 may extract a recommendation from the baseline database 136 to send to the medical professional to notify the medical professional of the cause of why the patient's data is outside the baseline levels and the action required to return the patient data back to within the baseline levels. For example, if there is a rapid drop in blood pressure the patient may be experiencing an unexpected bleeding event, and the recommendation may be to identify the bleeding event and stop the bleeding immediately, or the system can implement a stop instruction that stops the automated intervention steps to mitigate the bleeding event. Another example may be a warning the patient may go into shock since there is a severe drop in blood pressure and notify the medical professional of the warning with a recommendation to stop any blood loss, assist with breathing with mechanical ventilation, reduce heat loss, provide an IV or fluids, provide oxygen to the patient, provide medication to raise blood pressure, stop a hemorrhage, etc. depending on the type of surgery, what step in the procedure the patient is currently in, what the actions the medical professional was previously doing, etc. If it is determined that the sensor 152 data is not outside the patient's baseline data stored in the baseline database 136 the surgery module 130 determines, at step 412, if the surgery is complete. If it is determined that the surgery is not complete the surgery module 130 returns to sending a request for the sensor 152 data to the wearable device 140. For example, the surgery module 130 may be continuously polling for the medical professional to input that the surgery has been completed in the surgical robot 102 and if the input is not received the surgery module 130 returns to sending a request to the wearable device for the patient's sensor 152 data. If it is determined that the surgery is complete the surgery module 130 determines, at step 414, the thresholds for the patient's recovery period. For example, the medical professional may input the thresholds on the surgical robot 102 user interface 110 for the patient's recovery period and the medical professional inputs are sent to the surgical robot network 124 and stored in the threshold database 138. In some embodiments, the database may be updated depending on the stages of recovery, such as directly after the surgery has been completed, the bed rest period in which the patient remains in the hospital post-surgery, when the patient is first sent home, when the patient may be allowed to perform normal daily activities, etc. In some embodiments, the thresholds may be created through comparing the patient's entire profile to historical profiles to find similar patient's and extract the historical patient's thresholds. For example, the historical database may be filtered for patients with the same age, conditions, surgical procedure, location, ethnicity, sex, etc. and determine the closest match or closest matches to current patient to use the historical thresholds for the current patient's recovery period. The patient's recovery period, may be, for example, specific recovery periods such as 4 hours, 3 days, 1 week, 6 months, or ranges of recovery periods, such as, 4 to 8 weeks, 3 to 6 months, etc. It should be understood that the surgery module 130 may determine a plurality of thresholds associated with a plurality of recovery periods, e.g., hear rate between 50 bpm and 100 bpm for the first week, 50 bpm to 120 bpm for the second to fifth week, and 50 bpm to 150 bpm for the final six weeks of recovery. The surgery module 130 stores, at step 416, the thresholds in the threshold database 138. For example, the surgery module 130 stores the patient's name, the patient's ID or unique identifier, and the patient's threshold sensor 152 readings, such as a high pulse, low pulse, high blood pressure, low blood pressure, high SpO2, low SpO2, in the threshold database 136 in which if the sensor 152 goes above the high threshold or below the low threshold, a notification is sent. The surgery module 130 returns, at step 418, to the base module 126.

Functioning of the recovery module 132 will now be explained with reference to FIG. 5. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

This figure displays the recovery module 132. The process begins with the recovery module 132 being initiated, at step 500, by the base module 126. In some embodiments, the recovery module 132 may be initiated by a medical professional when the patient leaves the medical facility from having the medical procedure performed to track the patient's sensor 152 data after the surgery to monitor the recovery period. The recovery module 132 sends, at step 502, a request to the wearable device 140 for the sensor 152 data. For example, the recovery module 132 sends a request to the wearable device 140 for the sensor 152 data, such as the patient's pulse rate or heart rate such as beats per minute (bpm), the patient's blood pressure, and the patient's blood oxygen saturation levels or SpO2 levels. In some embodiments, the sensor 152 data may be collected at certain points during the day or randomly collected during the day. In some embodiments, the sensor 152 data may be continuously collected by the surgical robot network 124. In some embodiments, the sensor 152 data may include data from temperature sensors, blood glucose sensors, heart rate sensors, range of motion assessment sensors, electromyography (EMG) sensors, pedometer sensors, etc. In some embodiments, the sensor 152 data may be collected at certain points during the day or randomly collected during the day over the course of the recovery period. In some embodiments, the sensor 152 data may be continuously collected by the surgical robot network 124. The recovery module 132 receives, at step 504, the sensor 152 data from the wearable device 140. For example, the recovery module 132 receives the sensor 152 data from the wearable device 140. In some embodiments, the sensors 152 that are used by the wearable device 140 or sent by the wearable device 140 may be directly related to the patient's recovery process that may be a concern for the medical professionals, such as heart rate if the patient is having a stent implanted, the patient's mobility or movement if the patient is having back surgery, etc. In some embodiments, the surgery module 130 may store the received sensor 152 data in the patient database 134 and compare the data in the patient database 134 to the threshold database 138. The recovery module 132 compares, at step 506. the sensor 152 data to the threshold database 138. For example, the recovery module 132 compares the patient's received sensor 152 data, such as pulse, blood pressure, oxygen saturation levels, etc. to the thresholds stored in the threshold database 138. The comparison allows medical professionals to monitor, track, and react appropriately to the patient's data by receiving a notification if the patient's data is above or below the patient's threshold data. In some embodiments, the sensor 152 data received from the wearable device 140 may be sent to the surgical robot 102 user interface 110 to inform the medical professional of certain patient health parameters or medical information. In some embodiments, the threshold database 136 may include recommendation actions that a medical professional should take to return the patient's sensor 152 data back to above or below thresholds. In some embodiments, the threshold database 138 may be able to determine certain medical complications if the patient's health data falls into a certain range, such as if the patient's oxygen saturation levels drop below a certain level then the patient may be experiencing a pulmonary embolism in the event a clot separates from the vein and travels to the lungs which would require an emergency procedure for the patient. The recovery module 132 determines, at step 508, if the received sensor 152 data is outside of the thresholds stored in the threshold database 138. If it is determined that the received sensor 152 data is outside of the thresholds stored in the threshold database 138 the recovery module 132 sends, at step 510, a notification to the wearable device 140. For example, the recovery module 132 may send a notification to the user through the wearable device 140. In some embodiments, the recovery module 132 may send a notification to the medical professional to inform the medical professional of the patient's current condition, concerning sensor 152 data, or the patient's regression. In some embodiments, the recovery module 132 may extract a recommendation from the threshold database 138 and send the recommendation to the patient through the wearable device 140, such as time to move or perform physical therapy if the patient had back surgery. In some embodiments, the recovery module 132 may send a recommendation to the medical professional about the patient's medication usage, such as a side effect of the medication is a higher heart rate and the patient is experiencing a higher heart rate, etc. In some embodiments, the recovery module 132 can initiate a medication protocol that administers one or more tailored doses of medication responsive to the sensor readings and recovery data. If it is determined that the received sensor 152 data is not outside of the thresholds stored in the threshold database 138 the recovery module 132 determines, at step 512, if the patient's recovery period is complete. If it is determined that the recovery period is not complete the process returns to sending a request to the wearable device 140 for the sensor 152 data. For example, the recovery module 132 may extract the patient's recovery completion date from the patient database 134 and compare it to the current date, if there is not a match then the process returns to sending a request for the wearable device 140 sensor 152 data. If it is determined that the patient's recovery period is complete the recovery module 130 returns, at step 514, to the base module 126. For example, once the recovery period for the patient is complete the recovery module 132 returns to the base module to complete the process of monitoring the patient's data for the recovery period.

Functioning of the patient database 134 will now be explained with reference to FIG. 6. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

This figure displays the patient database 134. The database is created through the process described in the base module 126 in which the patient's profile data is stored and through the processes described in the baseline module 128, the surgery module 130, and the recovery module 132 in which the patient's sensor 152 data is collected and stored to either create a baseline for surgery or threshold for recovery as well as compared to the baseline database 136 and threshold database 138 to determine if any notifications or actions are required during the surgical procedure or recovery period. The database may contain the patient's name, a patient ID or unique identifier, a wearable ID, the install date or the date the patient began wearing the wearable device 140, the surgery date or the date the patient will have the surgical procedure, the end of recovery date or the date the patient's recovery period will end and thus no longer will be wearing the wearable device 140, the sensor 152 data collection date or the date the sensor 152 data was collected, the sensor 152 data collection time or the time in which the sensor data was collected, the patient's pulse rate or heart rate such as beats per minute (bpm), the patient's blood pressure, and the patient's blood oxygen saturation levels or SpO2 levels. In some embodiments, the sensor 152 data may be collected at certain points during the day or randomly collected during the day. In some embodiments, the sensor 152 data may be continuously collected by the surgical robot network 124. In some embodiments, the sensor 152 data may include data from temperature sensors, blood glucose sensors, heart rate sensors, range of motion assessment sensors, electromyography (EMG) sensors, pedometer sensors, etc. In some embodiments, the sensor 152 data may track patient data related to their surgical procedure, for example if a patient is having a disc replacement surgery the sensor 152 data may track the patient's daily movements before and after the surgery to determine if the patient is improving their mobility. For example, if the patient has stent implanted to open a clogged artery the sensor 152 data may collect the patient's heart rate, such as resting heart rate, before and after the procedure to determine if the patient's recovery is going as planned. In some embodiments, the medical professionals overseeing the patient's care may be able to view and analyze the patient's sensor 152 data to determine if the medications the patient is using for recovery are helping or if they are the underlying cause of certain sensor 152 readings. In some embodiments, the sensor 152 data may be used to detect early warning signs of potential serious conditions post-surgery, such as performing physical therapy too intensely, help reminder patients of post-surgical care routines, such as medications, exercise, nutrition, hydration, wound cleaning, etc., monitor medication reactions, etc.

Functioning of the baseline database 136 will now be explained with reference to FIG. 7. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

This figure displays the baseline database 136. The database is created in the process described in the baseline module 128 in which a baseline is created using the patient's sensor 152 data that is stored in the patient database 134 to be used during the patient's surgical procedure to determine if any of the patient's sensor 152 data goes over or below the created baseline. The database contains the patient's name, the patient's ID or unique identifier, and the patient's baseline sensor 152 readings, such as a high pulse, low pulse, high blood pressure, low blood pressure, high SpO2, low SpO2, in which if the sensor 152 goes above the high baseline or below the low baseline, a notification is sent. In some embodiments, the wearable device 140 may receive the notification. In some embodiments, the surgical robot network 124 may send the notification to the surgical robot 102 user interface 110 to inform the medical professionals. In some embodiments, the sensor 152 data received from the wearable device 140 may be sent to the surgical robot 102 user interface 110 to inform the medical professional of certain patient health parameters or medical information. In some embodiments, the baseline database 136 may include recommendation actions that a medical professional should take to return the patient's sensor 152 data back to the baseline readings. In some embodiments, the patient's vitals may be taken by the wearable device 140 and sent to the surgical robot 102. In some embodiments, the baseline database 136 may be able to determine certain medical complications if the patient's health data falls into a certain range, such as a huge drop in blood pressure may be caused by a bleeding event that needs to be stopped immediately, if the patient is about to go into shock due to a severe drop in blood pressure from blood loss and the blood loss needs to be stopped immediately, etc. In some embodiments, the database may be updated depending on the stages of surgery, such as the surgical robot 102 sending data back to the surgical robot network 124 and the patient's baselines change depending on whether they are being administered anesthesia, are being prepped for surgery, are undergoing the procedure, such as the first incision, implanting a stent, suturing the incision, etc., coming off the anesthesia, immediate recovery from the surgery, such as the first hour or two after the surgery is completed, etc.

Functioning of the threshold database 138 will now be explained with reference to FIG. 8. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

This figure displays the threshold database 138. The database is created during the process described in the surgery module 130 in which the thresholds may be created by a medical professional inputting the thresholds in the surgical robot 102 user interface 110 and sent to the surgical robot network 124 to be used during the patient's recovery period. The database contains the patient's name, the patient's ID or unique identifier, and the patient's threshold sensor 152 readings, such as a high pulse, low pulse, high blood pressure, low blood pressure, high SpO2, low SpO2, in which if the sensor 152 goes above the high threshold or below the low threshold, a notification is sent. The thresholds may be used to assist in the patient's recovery process to ensure the patient is recovery properly, performing the post-surgery tasks, such as performing exercise, taking the prescribed medication, etc. The patient's recovery period sensor 152 data may be analyzed by a medical professional to detect any anomalies or potential complications for the patient. In some embodiments, the wearable device 140 may receive the notification. In some embodiments, the surgical robot network 124 may send the notification to the medical professional to inform the medical professionals. In some embodiments, the threshold database 138 may include recommendation actions that a medical professional should take to return the patient's sensor 152 data back to in-between the thresholds. In some embodiments, the threshold database 138 may be able to determine certain medical complications if the patient's health data falls into a certain range, such as pneumonia, blood clots, deep vein thrombosis, which may lead to heart attacks, strokes, embolisms, etc., pulmonary complications, etc. In some embodiments, the database may be updated depending on the stages of recovery, such as directly after the surgery has been completed, the bed rest period in which the patient remains in the hospital post-surgery, when the patient is first sent home, when the patient may be allowed to perform normal daily activities, etc.

FIG. 9 shows an example of a computing device 700 and an example of a mobile computing device that can be used to implement computer-based aspects of the techniques described herein. The computing device 700 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 700 includes a processor 702, a memory 704, a storage device 706, a high-speed interface 708 connecting to the memory 704 and multiple high-speed expansion ports 710, and a low-speed interface 712 connecting to a low-speed expansion port 714 and the storage device 706. Each of the processor 702, the memory 704, the storage device 706, the high-speed interface 708, the high-speed expansion ports 710, and the low-speed interface 712, are interconnected using various busses, and can be mounted on a common motherboard or in other manners as appropriate. The processor 702 can process instructions for execution within the computing device 700, including instructions stored in the memory 704 or on the storage device 706 to display graphical information for a GUI on an external input/output device, such as a display 716 coupled to the high-speed interface 708. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 704 stores information within the computing device 700. In some implementations, the memory 704 is a volatile memory unit or units. In some implementations, the memory 704 is a non-volatile memory unit or units. The memory 704 can also be another form of computer-readable medium, such as a magnetic or optical disk.

The storage device 706 is capable of providing mass storage for the computing device 700. In some implementations, the storage device 706 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 704, the storage device 706, or memory on the processor 702.

The high-speed interface 708 manages bandwidth-intensive operations for the computing device 700, while the low-speed interface 712 manages lower bandwidth-intensive operations. Such allocation of functions is exemplary only. In some implementations, the high-speed interface 708 is coupled to the memory 704, the display 716 (e.g., through a graphics processor or accelerator), and to the high-speed expansion ports 710, which can accept various expansion cards (not shown). In the implementation, the low-speed interface 712 is coupled to the storage device 706 and the low-speed expansion port 714. The low-speed expansion port 714, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 700 can be implemented in a number of different forms, as shown in the figure. For example, it can be implemented as a standard server 720, or multiple times in a group of such servers. In addition, it can be implemented in a personal computer such as a laptop computer 722. It can also be implemented as part of a rack server system 724. Alternatively, components from the computing device 700 can be combined with other components in a mobile device (not shown), such as a mobile computing device 750. Each of such devices can contain one or more of the computing device 700 and the mobile computing device 750, and an entire system can be made up of multiple computing devices communicating with each other.

The mobile computing device 750 includes a processor 752, a memory 764, an input/output device such as a display 754, a communication interface 766, and a transceiver 768, among other components. The mobile computing device 750 can also be provided with a storage device, such as a micro-drive or other device, to provide additional storage.

Each of the processor 752, the memory 764, the display 754, the communication interface 766, and the transceiver 768, are interconnected using various buses, and several of the components can be mounted on a common motherboard or in other manners as appropriate.

The processor 752 can execute instructions within the mobile computing device 750, including instructions stored in the memory 764. The processor 752 can be implemented as a chipset of chips that include separate and multiple analog and digital processors. The processor 752 can provide, for example, for coordination of the other components of the mobile computing device 750, such as control of user interfaces, applications run by the mobile computing device 750, and wireless communication by the mobile computing device 750.

The processor 752 can communicate with a user through a control interface 758 and a display interface 756 coupled to the display 754. The display 754 can be, for example, a TFT (Thin-Film-Transistor Liquid Crystal Display) display or an OLED (Organic Light Emitting Diode) display, or other appropriate display technology. The display interface 756 can comprise appropriate circuitry for driving the display 754 to present graphical and other information to a user. The control interface 758 can receive commands from a user and convert them for submission to the processor 752. In addition, an external interface 762 can provide communication with the processor 752, so as to enable near area communication of the mobile computing device 750 with other devices. The external interface 762 can provide, for example, for wired communication in some implementations, or for wireless communication in other implementations, and multiple interfaces can also be used.

The memory 764 stores information within the mobile computing device 750. The memory 764 can be implemented as one or more of a computer-readable medium or media, a volatile memory unit or units, or a non-volatile memory unit or units. An expansion memory 774 can also be provided and connected to the mobile computing device 750 through an expansion interface 772, which can include, for example, a SIMM (Single In Line Memory Module) card interface. The expansion memory 774 can provide extra storage space for the mobile computing device 750, or can also store applications or other information for the mobile computing device 750. Specifically, the expansion memory 774 can include instructions to carry out or supplement the processes described above, and can include secure information also. Thus, for example, the expansion memory 774 can be provided as a security module for the mobile computing device 750, and can be programmed with instructions that permit secure use of the mobile computing device 750. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 764, the expansion memory 774, or memory on the processor 752. In some implementations, the computer program product can be received in a propagated signal, for example, over the transceiver 768 or the external interface 762.

The mobile computing device 750 can communicate wirelessly through the communication interface 766, which can include digital signal processing circuitry where necessary. The communication interface 766 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple ACCess), CDMA2000, or GPRS (General Packet Radio Service), among others. Such communication can occur, for example, through the transceiver 768 using a radio-frequency. In addition, short-range communication can occur, such as using a Bluetooth, WiFi, or other such transceiver (not shown). In addition, a GPS (Global Positioning System) receiver module 770 can provide additional navigation- and location-related wireless data to the mobile computing device 750, which can be used as appropriate by applications running on the mobile computing device 750.

The mobile computing device 750 can also communicate audibly using an audio codec 760, which can receive spoken information from a user and convert it to usable digital information. The audio codec 760 can likewise generate audible sound for a user, such as through a speaker, e.g., in a handset of the mobile computing device 750. Such sound can include sound from voice telephone calls, can include recorded sound (e.g., voice messages, music files, etc.) and can also include sound generated by applications operating on the mobile computing device 750.

The mobile computing device 750 can be implemented in a number of different forms, as shown in the figure. For example, it can be implemented as a cellular telephone 780. It can also be implemented as part of a smart-phone 782, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a LCD (liquid crystal display) display screen for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

In various implementations, operations that are performed "in response to" or "as a consequence of" another operation (e.g., a determination or an identification) are not performed if the prior operation is unsuccessful (e.g., if the determination was not performed). Operations that are performed "automatically" are operations that are performed without user intervention (e.g., intervening user input). Features in this document that are described with conditional language may describe implementations that are optional. In some examples, "transmitting" from a first device to a second device includes the first device placing data into a network for receipt by the second device, but may not include the second device receiving the data. Conversely, "receiving"

from a first device may include receiving the data from a network, but may not include the first device transmitting the data.

"Determining" by a computing system can include the computing system requesting that another device perform the determination and supply the results to the computing system. Moreover, "displaying" or "presenting" by a computing system can include the computing system sending data for causing another device to display or present the referenced information.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), peer-to-peer networks (having ad-hoc or static members), grid computing infrastructures, and the Internet.

The computing system can include clients and servers. A client and server are generally remote from each other and typically interact through a communication network. The relationship of client and server arises by virtue of computer programs running on the respective computers and having a client-server relationship to each other.

Further to the descriptions above, a user may be provided with controls allowing the user to make an election as to both if and when systems, programs or features described herein may enable collection of user information (e.g., information about a user's social network, social actions or activities, profession, a user's preferences, or a user's current location), and if the user is sent content or communications from a server. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over what information is collected about the user, how that information is used, and what information is provided to the user.

The functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The invention claimed is:

1. A method for monitoring a subject, the method comprising:
   receiving a sensor data set for the subject, the sensor data set comprising one or more patient metrics that indicate one or more biological conditions of the subject and that are based on signals produced by one or more biological sensors included in a wearable device on the subject, the sensor data received at a first time that is at least a pre-defined period of time ahead of a medical procedure scheduled for the subject;
   determining that a current time is within the pre-defined period of time ahead of the medical procedure scheduled for the subject;
   determining a set of patient metrics to use as a baseline data set for monitoring the subject during the medical procedure;
   using the baseline data to assess the subject's condition during the medical procedure;
   determining one or more procedure thresholds based on the baseline data, the one or more procedure thresholds include expected high and low values of the one or more patient metrics during the procedure;
   determining if a current time matches the procedure time; and
   sending, responsive to a determination that the current time matches the procedure time, a request to the wearable patient device for a procedure data set, the procedure data set including one or more patient metrics collected by the one or more biological sensors during the procedure time.

2. The method of claim 1, wherein the baseline data includes data acquired during the pre-defined period of time ahead of the medical procedure on the procedure date and data acquired before the procedure date.

3. The method of claim 1, further comprising:
   determining if the one or more patient metrics of the procedure data set are outside of the one or more procedure thresholds; and
   sending, responsive to a determination that one or more patient metrics are outside of the one or more procedure thresholds, instructions to a surgical robot, the instructions to the surgical robot include one or more intervention steps based on the one or more patient metrics that are outside of the one or more procedure thresholds.

4. The method of claim 3, wherein the one or more intervention steps include actuating one or more end effectors of the surgical robot to clamp an artery.

5. A method for monitoring a subject, the method comprising:
   receiving a sensor data set for the subject, the sensor data set comprising one or more patient metrics that indicate one or more biological conditions of the subject and that are based on signals produced by one or more biological sensors included in a wearable device on the subject, the sensor data received at a first time that is at least a pre-defined period of time ahead of a medical procedure scheduled for the subject;
   determining that a current time is within the pre-defined period of time ahead of the medical procedure scheduled for the subject;
   determining a set of patient metrics to use as a baseline data set for monitoring the subject during the medical procedure;
   using the baseline data to assess the subject's condition during the medical procedure;
   determining one or more procedure thresholds based on the baseline data, the one or more procedure thresholds include expected high and low values of the one or more patient metrics during the procedure;
   determining if a current time matches the procedure time; and
   sending, responsive to a determination that the current time matches the procedure time, a request to the wearable patient device for a procedure data set, the procedure data set including one or more patient metrics that correspond to a procedure type, the one or more metrics that correspond to the procedure type are collected during the procedure time.

6. The method of claim 5, further comprising:
determining if the one or more patient metrics of the procedure data set are outside of the one or more procedure thresholds; and
sending, responsive to a determination that one or more patient metrics are outside of the one or more procedure thresholds, instructions to a surgical robot, the instructions to the surgical robot include one or more intervention steps based on the one or more patient metrics that are outside of the one or more procedure thresholds.

7. The method of claim 6, further comprising:
repeatedly sending requests to the wearable patient device for an updated procedure data set responsive to the determination that one or more patient metrics are outside of the one or more procedure thresholds;
determining that the one or more patient metrics are within the one or more procedure thresholds; and
sending, responsive to the determination that one or more patient metrics are within the one or more procedure thresholds, instructions to a surgical robot, the instructions to the surgical robot including stop instructions for the one or more intervention steps.

8. The method of claim 6, wherein the wearable patient device activates and collects data from the one or more biological sensors based on the requested one or more patient metrics that correspond to the procedure type.

9. The method of claim 8, further comprising:
receiving surgical robot sensor data that is acquired by one or more sensors of the surgical robot;
comparing the surgical robot sensor data to the procedure data;
determining that the one or more patient metrics are within the one or more procedure thresholds; and
sending, responsive to the determination that one or more patient metrics are within the one or more procedure thresholds, instructions to a surgical robot, the instructions to the surgical robot include stop instructions for the one or more intervention steps.

10. A method for monitoring a subject, the method comprising:
receiving a sensor data set for the subject, the sensor data set comprising one or more patient metrics that indicate one or more biological conditions of the subject and that are based on signals produced by one or more biological sensors included in a wearable device on the subject, the sensor data received at a first time that is at least a pre-defined period of time ahead of a medical procedure scheduled for the subject;
determining that a current time is within the pre-defined period of time ahead of the medical procedure scheduled for the subject;
determining a set of patient metrics to use as a baseline data set for monitoring the subject during the medical procedure;
using the baseline data to assess the subject's condition during the medical procedure;
determining if a current time is after the procedure time on a procedure date;
determining one or more recovery thresholds based on the baseline data set and a procedure data set, the one or more recovery thresholds include high and low values of the one or more patient metrics; and
sending, responsive to a determination that the current time is after the procedure time, a request to the wearable patient device for a recovery data set, the recovery data set including one or more patient metrics that are collected after the procedure time.

11. The method of claim 10, further comprising:
determining if the one or more patient metrics of the recovery data set are outside of the one or more recovery thresholds; and
sending, responsive to a determination that one or more patient metrics are outside of the one or more recovery thresholds, instructions to a surgical robot, the instructions to the surgical robot include one or more intervention steps based on the one or more patient metrics that are outside of the one or more recovery thresholds.

12. The method of claim 11, further comprising:
repeatedly sending requests to the wearable patient device for an updated recovery data set responsive to the determination that one or more patient metrics are outside of the one or more recovery thresholds;
determining that the one or more patient metrics are within the one or more recovery thresholds; and
sending, responsive to the determination that one or more patient metrics are within the one or more recovery thresholds, instructions to a surgical robot, the instructions to the surgical robot include stop instructions for the one or more intervention steps.

13. The method of claim 10, further comprising,
determining that the one or more patient metrics are within the one or more recovery thresholds; and
sending, responsive to the determination that one or more patient metrics are within the one or more recovery thresholds, instructions to the wearable patient device to collect baseline data.

* * * * *